US010923216B1

(12) United States Patent
White et al.

(10) Patent No.: US 10,923,216 B1
(45) Date of Patent: Feb. 16, 2021

(54) HEALTH STATUS SYSTEM, PLATFORM, AND METHOD

(71) Applicant: TensorX, Inc., Vienna, VA (US)

(72) Inventors: N. Edward White, Austin, TX (US); G. Edward Powell, Nashville, TN (US); Van L. Marshall, Jackson, MI (US); Mark T. Lane, Franklin, TN (US); John C. Clerici, Vienna, VA (US)

(73) Assignee: TensorX, Inc., Nashville, TN (US)

( * ) Notice: Subject to any disclaimer, the term of this patent is extended or adjusted under 35 U.S.C. 154(b) by 0 days.

(21) Appl. No.: 16/900,803

(22) Filed: Jun. 12, 2020

(51) Int. Cl.
*G16H 10/40* (2018.01)
*G16H 10/60* (2018.01)
*G16H 50/20* (2018.01)
*G16H 50/50* (2018.01)
*G07C 9/37* (2020.01)
*G07C 9/38* (2020.01)
*H04L 29/06* (2006.01)
(Continued)

(52) U.S. Cl.
CPC .......... *G16H 10/40* (2018.01); *A61B 5/1171* (2016.02); *A61B 5/1172* (2013.01); *A61B 5/4842* (2013.01); *G06F 16/2365* (2019.01); *G07C 9/37* (2020.01); *G07C 9/38* (2020.01); *G16H 10/60* (2018.01); *G16H 50/20* (2018.01); *G16H 50/30* (2018.01); *G16H 50/50* (2018.01); *H04L 9/3268* (2013.01); *H04L 63/0428* (2013.01); *G06K 9/00711* (2013.01); *G06Q 50/265* (2013.01); *G16H 50/80* (2018.01); *H04L 2209/38* (2013.01)

(58) Field of Classification Search
CPC ........ G16H 10/40; G16H 10/60; G16H 50/20; G16H 50/30; G16H 50/50; G16H 50/80; A61B 5/117; A61B 5/1171; A61B 5/1172; A61B 5/4842; H04L 63/0428; H04L 9/3268; H04L 2209/38; G06K 9/00711; G06Q 50/265
See application file for complete search history.

(56) References Cited

U.S. PATENT DOCUMENTS 7,092,839 B2 * 8/2006 Buote .................... G16H 10/40
                                                  702/123
8,577,697 B2 * 11/2013 Demopulos ............ G06Q 50/24
                                                  705/3
(Continued)

*Primary Examiner* — Linglan E Edwards
(74) *Attorney, Agent, or Firm* — John K. Harrop

(57) ABSTRACT

A health status platform includes a receiving component that receives a test result a test of a biological sample collected from a human patient. The test result includes an indication of a presence of an infectious disease in the patient, and an identification and a verification of the patient. The platform includes a certificate component that issues a certificate of origin of the biological sample; and a data merging component that cooperates with a venue access manager that controls access to a venue. The data merging component implements a distributed ledger system that stores encrypted test results of the patient and the identification and verification of the patient, and an end-to-end encryption system that receives an encrypted venue access request from a venue access manager, decrypts the access request, determines if an access request is valid, and if valid, provides an encrypted certificate of origin to the venue access manager.

22 Claims, 13 Drawing Sheets

(51) Int. Cl.
*H04L 9/32* (2006.01)
*G06F 16/23* (2019.01)
*A61B 5/1172* (2016.01)
*A61B 5/1171* (2016.01)
*A61B 5/00* (2006.01)
*G16H 50/30* (2018.01)
*G06K 9/00* (2006.01)
*G16H 50/80* (2018.01)
*G06Q 50/26* (2012.01)

(56) References Cited

U.S. PATENT DOCUMENTS

| | | | |
|---|---|---|---|
| 8,679,012 B1* | 3/2014 | Kayyali | A61B 5/0488 600/301 |
| 2014/0207489 A1* | 7/2014 | Wartena | G06F 19/00 705/3 |
| 2017/0024520 A1* | 1/2017 | Michon | G06Q 50/24 |

* cited by examiner

US 10,923,216 B1

HEALTH STATUS SYSTEM, PLATFORM, AND METHOD

BACKGROUND

Management of federally protected personal information including but not limited to data governed by the Health Insurance Portability and Accountability Act (HIPPA), the Family Educational Rights and Privacy Act (FERPA), and others pose risk for institutions responsible for maintaining privacy. Several technological innovations have been created to protect information owned by healthcare providers, universities, and financial institutions. There have been changes in the laws regarding some of these regulated data. For example, there are new regulations around health record and transportability for Personal Health Information (PHI). Likewise, in the presence of COVID-19, there have been policy discussions around concepts such as contact tracing.

The threats, including infection, resulting from an epidemic, pandemic, bio-terrorism or biological warfare are driving organization to consider restricting access to their venues, modes of transportation, and activities to individuals that have been tested and are, within the limits of the test: sensitivity, specificity, surety, etc. infection free and/or are immune to infection. One approach to accomplish this is to test at the point of entry by clinical personnel. For example, it was recently announced during the SARS-CoV-2 pandemic that visitors to the White House were screened for the virus prior to being allowed to meet with the President. In this case each test is performed on site and the results reported directly to the person being tested by those conducting the test. Each person's nose or throat is swabbed and the resulting bio-sample is analyzed for indications of infection. In some applications, body fluids, blood or mucus may be sampled/tested, including, for example, to test for sexually-transmitted diseases and other diseases. These onsite tests generally take 15 to 20 minutes from sample collection to result.

Similarly, other sites such as nursing homes, hospitals and meat processing facilities are regularly testing employees before allowing them access to the premises. In all these cases the test results are single use at that location and are not generally transferable or reusable at other settings.

Several entities are moving rapidly to create the onsite and point of care infrastructure necessary to support broad application of testing at locations like airports, sporting and entertainment venues, vacation rentals, car rentals, taxis, ride share, and others.

In addition, diagnostic manufacturers are working on home testing kits so that persons can test themselves in the privacy of their home prior to departing for an event or series of events. In these cases, the home test could lead to expedited medical care or direct distribution of pharmaceuticals like "TamiFlu" in the case of influenza.

There is a tension between the public health interest in ensuring a venue does not pose a health risk and the privacy associated with personal health information. There is a need for an infrastructure to maintain the status of all these test results in such a way that the test results can be provided at different locations to the benefit of the attendees, without being detrimental to the person being tested. Moreover, access to the test results could be managed by various parties from the person being tested, to an employer, or an owner of a venue.

For example, when a user has been tested and shown not to be infected with any single or multiple infectious diseases, that disease free status need not only be used once, it could provide access to any number of venues for a specified period of time under the control of the user.

SUMMARY

A health status method executed by a processor includes receiving from a test system, by the processor, a representation of biological sample data of a human sample collected from a human user and analyzed by the test system for identification of a presence of an infectious disease, and identification information identifying the user. The biological sample data includes the indication of the presence of the infectious disease; a time and date of sample collection of the biological sample; and an identification of the test system. The information identifying the identity of the user includes an attestation of the identification of the user recorded in conjunction with collecting the biological sample of the user. The method further includes registering and storing the biological sample data in a central storage; associating the attestation of the user with the biological sample of the user; and generating a certificate of association between the attestation of the user and the biological sample of the user. Generating the certificate includes analyzing the attestation of the user, based on the analysis, verifying that the collected biological sample was obtained from the identified user, and assigning a time to live for the certificate. The method then includes receiving from a venue, an access request for the user to access the venue; determining the access request is for a time within the period of the time to live; and providing the certificate of association to the venue.

In an aspect the attestation of the user is a representation of a biometric sample of the user, the biometric sample of the user obtained in conjunction with collection of the biological sample, the representation generated by a processing device from the obtained biometric sample of the user. The biometric sample may be one or more of a thumb print set recorded from the user, a retina scan recorded from the user, and a DNA sample obtained from the user and analyzed.

In an aspect, the attestation is a video of the user submitting the biological sample, and the video is executed under control of a biological sample routine executed to obtain the biological sample. In a further aspect, the video is witnessed by a trusted agent and the attestation is supplied by the trusted agent.

A health status platform includes a receiving component, having a processor and a data store, that receives a test result a test of a biological sample collected from a human patient. The test result includes an indication of a presence of an infectious disease in the patient, an identification and a verification of the patient from whom the biological sample was collected, a location, time and date of sample collection, and an identification of test of the biological sample. The platform further includes a certificate component that issues a certificate of origin of the biological sample; and a data merging component that cooperates with one or more venue access managers that operate to control access to corresponding venues. The data merging component implements a distributed ledger system that stores encrypted test results of the patient and the identification and verification of the patient, and an end-to-end encryption system that receives encrypted venue access requests from a venue access manager, decrypts the access requests and determines if the access request is valid or not valid, and for valid access requests, provides an encrypted certificate of origin to the venue access manager. In an embodiment, the health status platform may be used to detect infection from a variety of diseases, including respiratory diseases and blood-borne diseases; the platform may be used, for example, to test for infection from sexually-transmitted diseases, influenza, and COVID-19.

A health status system includes a distributed computing system that in turn includes a data store, one or more processors, and wireless and wired communication equipment, the data store including non-transitory-computer-readable media storing a program of instructions that, when executed by a processor, cause the processor to receive from a test system a representation of biological sample data of a human sample collected from a human user and analyzed by the test system for identification of a presence of an infectious disease, and identification information identifying the user. The biological sample data includes the indication of the presence of the infectious disease; a time and date of sample collection of the biological sample; and an identification of the test system. The information identifying the identity of the user includes an attestation of the identification of the user obtained in conjunction with collecting the biological sample of the user. The processor further executes to store the biological sample data in the data store; associate the attestation of the user with the stored biological sample data of the user; and generate a certificate of association between the attestation of the user and the stored biological sample data of the user. To generate the certificate of association, the processor analyzes the attestation of the user, based on the analysis, verifies that the collected biological sample data were obtained from the identified user, and assigns a time to live for the certificate. The processor also receives from a venue, an access request for the user to access the venue; determines the access request is valid; and provides the certificate of association to the venue.

DESCRIPTION OF THE DRAWINGS

The detailed description refers to the following figures in which like numerals refer to like items, and in which.

DETAILED DESCRIPTION

Figure 1:
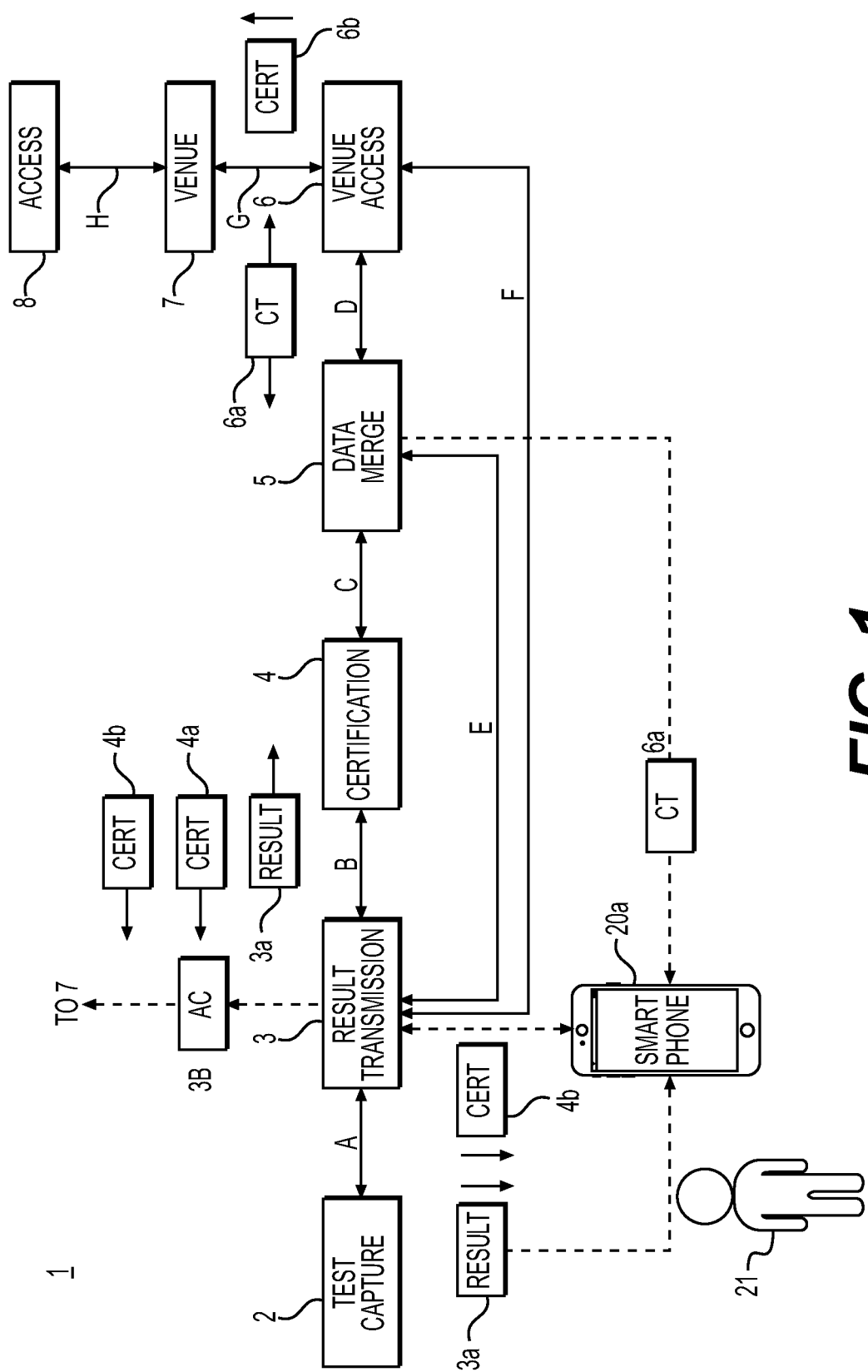
FIG. 1 illustrates an example Health Status System.

When a person is administered a test for an infectious disease, at the user's request/authorization, the test results can be forwarded via the Internet or other communications network to a health status service provider. The health status service would confirm that the person submitting the test results has been tested, and in the case of a positive test is eligible for and in need of available medical care, or in the case of a negative test the person may be allowed to access restricted areas or services. In the case of an antibody test, the result could also indicate immunity to a particular disease for a period of time.

The test being administered can be performed at a medical facility or point of care, at a third party testing location (the entrance to one's place of employment, an educational facility an entertainment venue, a testing kiosk, etc.), or it could be performed at home or other private location by the person themselves taking the test. In each case security and privacy of the test results must be maintained. Each test, whether at a remote facility or in private setting, will have a unique test identification (ID) code. The ID code is assigned by the test kit manufacturer, the testing facility, or the person administering the test. The test ID code is unalterable and is single use. It might be encrypted and written to a public ledger via a technique like blockchain.

For tests performed at a medical facility, point of care or third-party testing location, the test results can be verified as belonging to the individual by the person performing the test. For tests done at a private location, several techniques can be used to verify that the tests results belong to the individual submitting the test.

Private test verification techniques. Tests can be verified in at least the following three ways: user certified techniques; test identification techniques, and remote witness techniques.

User certified techniques. These methods of test verification involve a user submitting some form of identification in the form of a password, fingerprint, iris scan, voice scan, facial recognition, etc. along with an attestation that they are in fact the person for whom the test results apply. The user might also submit a photo or video of themselves taking the test along with the test results or use other methods of identity verification.

Test identification techniques. These methods of test verification involve collecting information from the test bio-sample itself. DNA matching, biomarker profile matching, or other techniques that are unique to an individual that can be discerned by the testing system can verify the identity of the individual and compared to a sample, profile, bio-signature or other information that is on record for that individual. For example, a user can create an initial bio-profile or bio-signature that is stored online for comparing future test samples against so as to verify the identity of the person submitting the test results.

Remote witness techniques. Tests performed in a private location can be witnessed by a third party via a video teleconference or telemedicine application. The third party can be a health care professional, a government employee or the equivalent of a medical notary. The third party can verify that a test with a particular id code was conducted by the person submitting the test results. The third-party certification can be merged with the test results when sent to the health status service provider.

The health status service (HSS) operating a health status platform (HSP) receives test results and validates/certifies that these results belong to a particular person. The HSP performs the following functions:

Maintains a user account. The user account is established by the user, is password protected, has a unique ID and stores user profile information that may include biometric markers, signatures or other identifiers Receives a test result from a user. Test results can be sent from a point of care facility, a third-party testing facility or a home test system to a health status system provider (HSSP). Information is sent and received in an encrypted format or may be protected with blockchain techniques to ensure complete privacy of the user test results information.

Maintains a secure copy of the user's test results.

Establishes a timestamp for the test results. Some test results like antigen tests are testing for active infection and may only be valid for a number of hours. Other test types that are antibody tests may show long-term immunity to an infection and may be valid for months or years. As a result, the HSSP would establish a timestamp for the test results.

Establishes a quality of certification of the test results. Based on the various ways that a test can be certified the HSSP will assign a quality of certainty that the test results belong to the person submitting the test results. For example, in the lowest level of certification the user submitting the results attests that these results belong to them. This is the lowest level of certification because a user could submit unverified false information that the test results actually belonged to them. In the highest level of security, a DNA signature could be matched to validate that the test results belong to the user. Various levels of certification can be established in between where third parties validate the test results as belonging to the user.

Provides test results, test type, timestamp and level of certification to third parties with the user's permission. In some cases, the level of certification is not required.

Logs all interactions where health status was provided to third parties and user authorizations. This information can be used to provide a health history over time for the user.

Disclosed herein are systems, platforms, and methods that provide safe and secure transmission of health-related data. The systems and methods ensure validity of health data. The systems and methods provide a convenient and tamper-proof data exchange. As such the systems and methods, and corresponding techniques and architectures, disclosed herein, including but not limited to receiving and using asset and/or write permissions, locking assets, instantiating assets, and/or implementing a multiple tier permission detail a technical solution (implementing interoperability) to a technical problem (non-interoperability). This technical solution improves the operation of the underlying hardware—previously non-interacting hardware systems provide an efficient platform by which to interact. Furthermore, the aforementioned features provide improvements over existing market solutions by providing a technical solution allowing greater interoperation between hardware systems as compared to existing interoperation techniques.

FIG. 1 represents a general approach. In FIG. 1, system 1 includes a test capture and analysis component 2, a health status transmission component 3, a certification component 4, a data merging component 5, and a venue access component 6. In an embodiment, the test capture component 2 and health status transmission component 3 communicate over interface A to cooperatively allow administration of a health test of a user (not shown), analysis of the test, and generation of a test result by the test capture and analysis components 2. The component 2 may supply the results of a test to the component 3 over the interface A. In an aspect the test capture and analysis component 2 and the health status transmission component 3 may be combined in a single hardware device. In another aspect, the components 2 and 3 may be stand-alone hardware devices. In an aspect, some functions of the health status transmission component 3 may be embodied in another component, such as smart phone 20a, or similar device, for example.

In an embodiment, the test capture and analysis component 2 may be implemented at a kiosk. The kiosk could be located at a specific venue, such as at the entrance to a theme park, a stadium, or an airport terminal. Alternately, the kiosk could be located at a business entrance, and may be used by employees of the business and visitors to the business. Alternately, the kiosk could be located at a pharmacy or at a medical clinic. In this embodiment, the kiosk also may provide some or all the functions of the health status transmission component 3.

In an embodiment, the test capture and analysis component 2 is, or includes a specific health test kit, such as a test kit for testing a user for possible infection from COVID 19 or other relevant diseases potentially affecting public health. Such a test kit may be a small, portable device configured to cooperate with the health status transmission component 3. The test kit includes mechanisms, such as swabs, to acquire a sample from the user, analyze the sample, and provide test result 2a to the health status transmission component 3 over the interface A.

In an embodiment, the user 21 may employ the test kit to self-perform a health test, such as when at home or other private setting.

In another embodiment, such as when implemented at a kiosk, the test capture and analysis component 2 may be configured to perform different types of health tests, such as for COVID 19, influenza, and/or other relevant diseases potentially affecting public health.

The health status transmission component 3 may include mechanisms to control operation of the test capture and analysis component 2. For example, when implemented in the smart phone 20a, the component 3 may include or be in communication with an application (not shown) of the smart phone 20a, and the application may initiate analysis by the component 2, may provide data related to the user to the component 2, and may provide security for the test result 2a (e.g., encryption). Such security processes, and associated security mechanisms are described in more detail herein. Following any processing at the component 3, the test result 2a and any associated data may be sent, encrypted, or otherwise protected, as secure test result 3a to the certification component 4.

The certificate component 4 receives the secure test result 3a over interface B from the health status transmission component 3. In an aspect, the components 3 and 4 may be combined into a single unit or single hardware device. In another aspect, the components 3 and 4 may be co-located such as at a medical clinic. In yet another aspect, the components 3 and 4 are separated and may communicate over a wireless communications network. The transmission mechanism, when components 3 and 4 are not combined in a single unit, may include any suitable digital data exchange mechanism. A process of secure test result 3a transmission is described in more detail herein.

In an embodiment, the certificate component 4 functions to process a secure test result 3a and from the test result processing, generate a digital certificate 4a attesting to the acceptability of the test result for one or more purposes. Those purposes may include, for example, allowing the user 21 whose health is represented by the digital certificate 4a to access one or more venues that are associated with venue access component 6. The digital certificate 4a also may include the test result as well as all information provided in the secure test result 3a. The digital certificate 4a may include the date and time of sample collection, the test kit identification, including manufacturer and date of manufacture, test type, and a unique serial number of the test kit. The digital certificate 4a further may include a time to live for the test result, such as, for example, 24 hours, one week, etc. Upon reaching the time to live, the digital certificate 4a may be disabled, deleted, and/or flushed from any existing storage in the system 1. Alternately, the digital certificate may simply be permanently disabled or deactivated such that it no longer may be used in the system 1 to allow user 21 to gain access to a venue. The digital certificate 4a also may include a quality value. The quality value may be based on the type of test and the identity of the test kit. The quality value further may be based on the process or modality by which the sample is collected and the test result is produced from the sample. The quality value still further may be based on the degree of security, or confidence, in the reliability of the test result. In this regard, a sample collection and analysis modality that provides as close as possible to absolute verification that the user 21 submitting the sample is in fact the user sampled may produce a highest quality value. For example, a test sample collected by a medical professional at a medical clinic and processed to produce a test result by the medical professional may have a highest value. A test sample collected at a kiosk and analyzed at the kiosk may have a high value. A test sample collected by user 21 and applied to a home test kit may have a medium value. Other quality factors and quality rating systems may be employed. A digital certificate 4a with a highest quality may allow user 21 access to any venue while a digital certificate 4a with a medium quality value may allow access to certain venues but not others. In an embodiment, the user 21 may be provided with the quality value required by a venue and the quality value a specific test sample collection and analysis modality will produce, thereby allowing the user 21 to select a modality that should produce the required or desired quality value.

In an embodiment, the certificate component 4 may provide the digital certificate 4a to the component submitting the secure test result 3a. For example, if the submitting component is the smart phone 20a of user 21, the certificate component 4 may transmit the digital certificate 4a to the smart phone 20a. If the test result submitting component is a kiosk, the certificate component 4 may provide the digital certificate 4a to an address input to the kiosk by the user 21; for example, an email address of the user 21. Alternately, the certificate component 4 may provide the digital certificate 4a for printing at the kiosk. When printed, the printed digital certificate 4a may include a tamper-proof RFID (e.g., a read-once RFID). In any aspect, the digital certificate 4a may include an indication readable by the user 21 as to the quality value (e.g., highest, high, medium).

In another embodiment, the certificate component 4 produces a digital certificate 4b with a tamper-proof reference. The reference then may be used to look up and retrieve data such as that incorporated in the digital certificate 4a. The user 21 may employ the digital certificate 4b in its digital form or in a printed form. For example, the user 21 may provide the digital certificate 4b on the user's smart phone display, where the digital certificate may be read at a venue access point.

In an embodiment, the certificate component 4, or aspects of the certificate component 4, may be implemented in a cloud-based system. For example, the component 4 may maintain active as well as deactivated digital certificates 4a, 4b in a cloud storage facility.

As noted herein, the components 3 and 4 may be combined on a single hardware device. In an embodiment, the certificate component 4 may be implemented on the smart phone 20a (or another smart device operated by the user 21, such as a tablet or computer). In this embodiment, digital certificates 4a are stored on the smart phone; phone 20a, where they remain active until expiration of the assigned time to live. When implemented on the smart phone 20a, the component 4 may be a component of the application 22. When implemented on a computer, the component 4 may be a component of a non-transitory computer-readable medium storing a program of instructions (not shown in FIG. 1).

When implemented as a service separate from the health status transmission component 3 (e.g., as a cloud-based service), the certificate component 4 may transmit the digital certificates 4a, 4b to the data merging component 5 over interface C. In an aspect, such transmission may require authorization from the user 21. In another embodiment, the user 21 may operate the smart phone 20a, or other smart device, to transmit the digital certificates 4a, 4b to the data merging component 5 over interface E.

The data merging component 5 may produce a certified ticket 6a that the user 21 may employ to access a specific venue 7. However, the certified ticket 6a need not be a "ticket" in its common use. For example, when user 21, when user 21 employs the HSS 1 to schedule a ride-sharing service, the "certified ticket 6a" may be, instead, an electronic file or other mechanism appropriate for a ride sharing service. The data merging component 5 may produce the certified ticket 6a by merging data 6b from the venue access component 6 with a digital certificate 4a, having acquired the digital certificate 4a from the certificate component 4 or the health status transmission component 3. The data merging component 5 may generate the certified ticket 6a when requested or authorized to so by the component 3.

The venue access component 6 may communicate directly with the health status transmission component 3 over interface F and/or with the data merging component 5 over interface D. The venue access component 6 may communicate with one or more venues 7, each of which may control one or more venue access points 8. In an aspect, a venue access point is a gate or entry to a venue 7. The venue access point 8 may be provided with an access control device including, but not limited to a processor-controlled turnstile. The access control point 8 may be configured to allow user 21 to access the venue based on satisfactory reading to a certified ticket 6a independent of how the certificate is read or access is controlled.

In an embodiment, the venue access component 6 may be a component of a venue 7 and further may be implemented at a venue access point 8. In another embodiment, the venue access component acts as a service for multiple venues 7, none of which need be related to each other. For example, one venue 7 could be an airport and a second venue 7 could be a theater.

In an embodiment, the certified ticket 6a may be produced by the venue access component 6 based on inputs received from the test result, or health status transmission component 3 and/or the data merging component 5. In an aspect, the component 3 may provide a digital certificate 4a to the venue access component 6. In another aspect, the component 3 may provide the venue access component 6 with authorization and a mechanism to acquire a digital certificate 4a from the data merging component 5. In yet another aspect, the component 3 may provide the venue access component 6 with authorization and a mechanism to acquire a certified ticket 6a from the data merging component 5.

In the aspect in which the component 3 provides the venue access component 6 with authorization and a mechanism to acquire a digital certificate 4a from the data merging component 5, the venue access component may generate the certified ticket 6a.

The health status transmission component 3 may communicate directly with a venue 7 to request access to the venue 7; that is, to buy a ticket from the venue 7 so as to allow the user 21 to enter the venue 7. Access request 3b may include an implicit or explicit authorization to release the user's digital certificate 4a. Alternately, the access request 3b may include the digital certificate 4a. The venue 7 may pass that access request 3a to the venue access component 6, which may in turn pass the access request to the data merging component 5.

In an embodiment, the processes executed by the components 5 and 6 may result in a user device such as smart phone 20a being provided with a certified ticket 6a. Alternately, the certified ticket 6a may be provided to the venue 7 for pickup by the user 21. In this alternative, the certified ticket 6a may be in digital form (i.e., the certified ticket 6a) or may be printed at the venue 7 and acquired thereat by the user 21 (e.g., will call), when the user 21 supplies the venue 7 with a satisfactory certification 6b, which may be a separate digital file. A satisfactory certification 6b is described in more detail herein.

Figure 2:
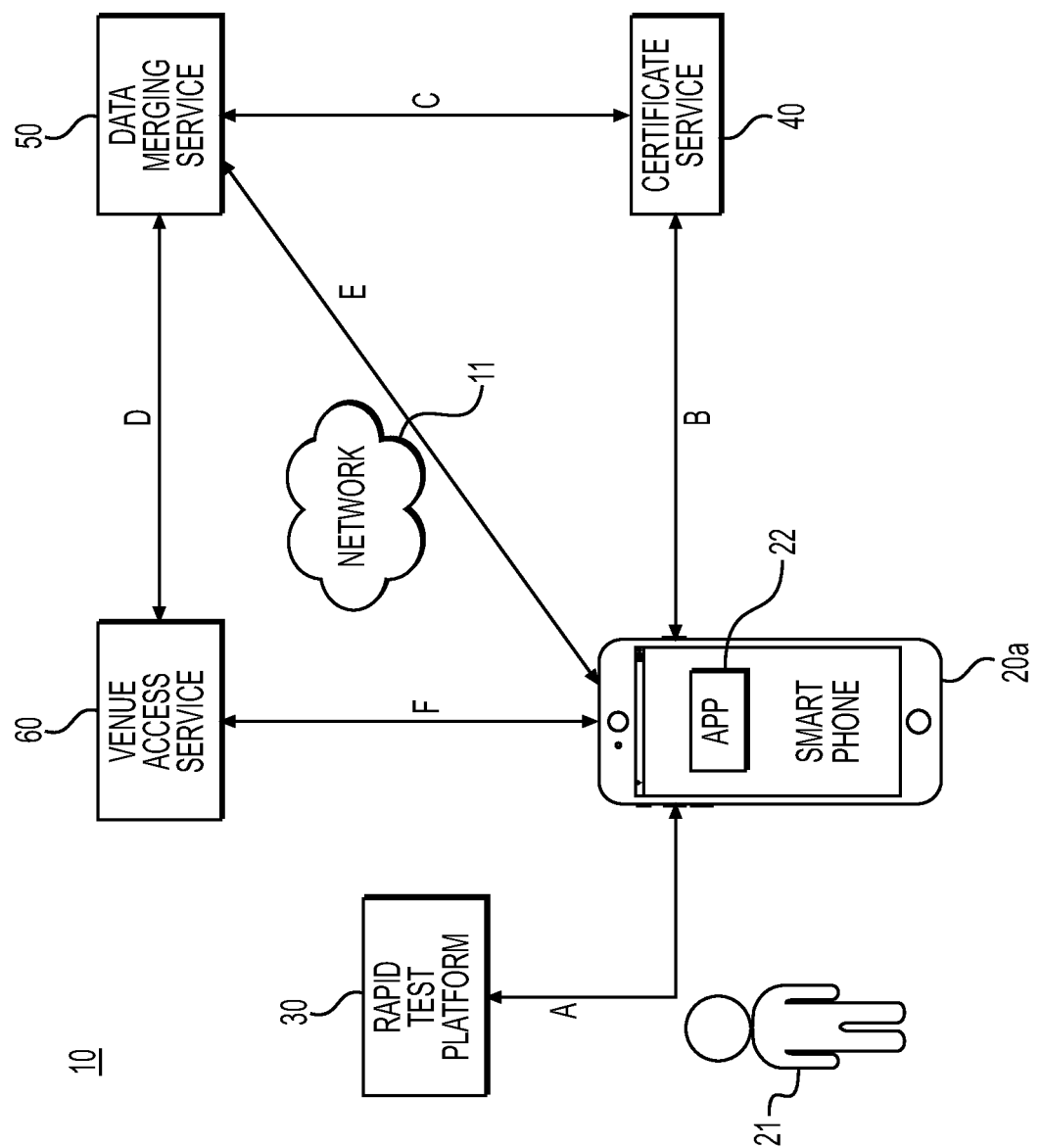
FIG. 2 illustrates another example Health Status System.

FIG. 2 illustrates an embodiment of a Health Status System (HSS) that executes aspects of the system of FIG. 1. The HSS embodiment of FIG. 2 may be executed in part at a home of a user, or at another private location of the user, such as at a hotel room. Thus, in one aspect of this embodiment, the user may not interact directly or indirectly with any authenticating authority such as a medical professional, a notary, or other person. In a second aspect, however, the user may interact with such an authenticating authority.

In FIG. 2, Health Status System (HSS) 10 includes a personal device 20 operable by user 21. The personal device 20 may be used in conjunction with rapid test platform 30. The HSS 10 further includes certificate service 40, data merging service 50, and venue access service 60. These and other components of the HSS 10 may communicate over communications network 11.

In an aspect, the personal device 20 may be a smart device. Such a smart device may include a program of instructions executed by a smart device processor to support operations of the HSS 10. Alternatively, the smart device may include an HSS application 22 that functions to support operations of the HSS 10. The smart device may be a smart phone, tablet, or computer, for example. In another aspect, the personal device 20 may be a dedicated device. Such a dedicated device may include a program of instructions that are executed by a processor on the dedicated device to support operations of the HSS 10. Alternately, such a dedicated device may include an application specific integrated circuit (ASIC) programmed to support operations of the HSS 10. The personal device 20 may be capable of wired and wireless communication, including Bluetooth communication, with other devices or components of the HSS 10, and devices and components outside the HSS 10. In an aspect, the personal device 20 is smart phone 20a.

Wired communications among entities in the HSS 10 may occur over a public network such as A PSTN and/or over a dedicated wired network. A dedicated wired network may be a secure wired network. Such wireless communications may occur over a wireless communication network 11, which may be a wide area network (i.e., the Internet) separated from the HSS 10, and/or over a local area network (LAN), which may be implemented by components of the HSS 10.

The communications network 11 may be or may include a virtual private network (VPN) implemented separately from the HSS 10 or as an adjunct to the HSS 10.

The HSS 10 may include one or more rapid test platforms 30. As disclosed herein, such test platforms 30 may be dispersed throughout the HSS 10. The test platforms 30 may be capable of wired communications and wireless communications over the communications network. Operation of the test platforms 30 is described in more detail herein. However, as shown in FIG. 1, a test platform 30 may be in wired or wireless communication, including Bluetooth, with personal device 20. In operation, a test platform 30 may be in close proximity to the personal device 20; that is, for example, within a few feet of the personal device 20, such as within 12 feet. In an aspect, the personal device 20 may include a camera (not shown in FIG. 2) that is used as an element of the operation of the HSS 10, where the camera provides a view of the test platform 30, which is made possible by such close proximity.

In an aspect, a test platform 30 is a one-time use device. The platform 30 may be battery powered. The platform 30 may be implemented to perform a specific test or to perform one or more similar tests. For example, a test platform 30 may be implemented to test for influenza, to test for COVID-19, or to test for both. The test platform 30 includes all components needed to execute a test, such as a test for COVID-19, and to provide the results of the test to the personal device 20.

In another aspect, the test platform 30 may be capable of multiple uses. In a respect, the test platform 30 may be capable of multiple uses by a same user 21. In another respect, the test platform 30 may be capable of use by multiple users 21.

In addition to providing the test result to the personal device 20, the test platform 30 may provide a unique identification. In an aspect, the unique identification may provide one or more of a unique test platform serial number, an identification of the test (e.g., for COVID-19, including the specific test type), test platform manufacturer and date of manufacture (e.g., in case of a shelf-life), and date and time of test. In an aspect, the test platform 30 may provide the geographic location of the test platform. In a respect, the test platform 30 may query the personal device 20 to obtain the geographical location. In another respect, the test platform 30 may obtain the geographical position from an existing but separate GPS system.

When the test platform 30 is used for multiple tests, the test platform 30 may employ a counter, and may provide the counter value with the unique identification.

The test platform 30 may interface with an application 22 implemented on the personal device 20. The application 22 may be acquired from an online store, for example, and may be intended for use with the specific test platform 30.

In an aspect, the application 20 may implement security measures to first verify the validity of the test, second protect the test result from corruption, hacking, or other attack, and third preserve the privacy of the user 21. For example, the application 22 may implement an end-to-end encryption routine. Such security measures are described in more detail herein. The application also may present the test results (or a summary of the test results) for display to the user 21 on a screen or other graphical user interface of the personal device 20.

The personal device 20 may communicate directly with each of the services 40, 50, and 60 in a manner similar to communications described with respect to FIG. 1, and for the same or similar purposes. Thus, operations of the HSS 10 may result in the user 21 acquiring a certified ticket (similar to certified ticket 6a of FIG. 1). In this first aspect of the embodiment of FIG. 2, such certification may be based on one or more actions taken by the user 21. In one action, the user 21 digitally signs an affidavit that it was the user 21 whose sample was taken and tested. A false attestation may result in civil or criminal penalties. The user 21 may submit a biometric sample with the test sample. The biometric sample could be a retina scan or thumbprints, for example. Other biometric samples may be submitted. At a venue point of entry, the user 21 would submit the same biometric sample type to confirm the user's identity. Alternatively, the HSS 10 could submit to the venue not only the test certificate for the user 21, but also the biometric signature of the user 21. In one action, the user 21 could submit thumbprints at a turnstile or point of entry, and the certificate service 40, or other component of the HSS 10, would then immediately send the certificate from the user 21 along with validity of the user's biometric signature, allowing fast and immediate access for the user 21. A thumbprint sample collection could be implemented in the application 22, for example, using a thumbprint collection window displayed on a screen to the smart phone 20a. In a further aspect, the smart phone 20a, equipped with a camera, may capture an image of the user 21 when the thumbprints are collected. The application 22 then would execute to cause the smart phone 20a to transmit the thumbprints and the image, along with the test results, to the certificate service 40.

Figure 3:
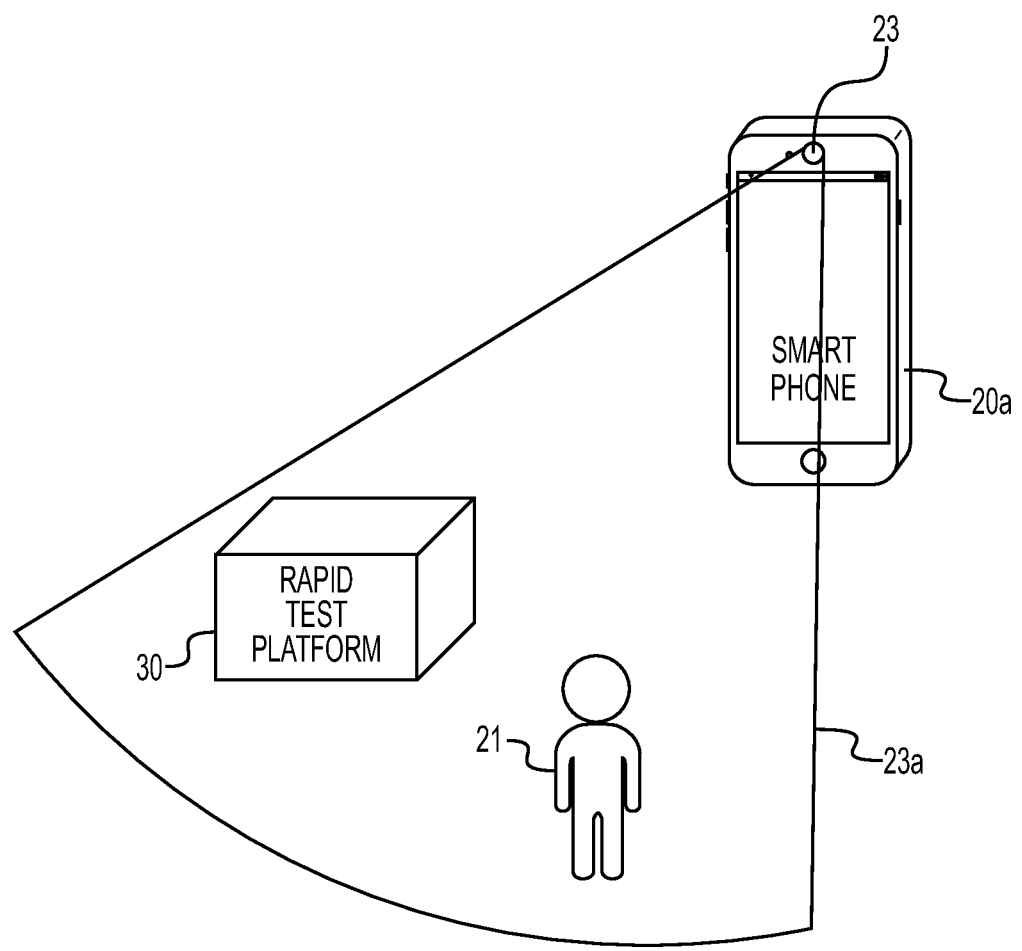
FIG. 3 illustrates a sample validation operation executed by components associated with the example Health Status Systems of FIGS. 1 and 2.

The second aspect of the embodiment of the HSS 10 may incorporate additional authentication elements, as shown in FIG. 3. In FIG. 3, the user 21 is instructed to arrange the test kit 30 and the smart phone 20a so that the camera 23, with field of view 23a, may capture still frames or a video to record the sample collection. The recorded images then are included with the test results sent to the certificate service 40.

Figure 4:
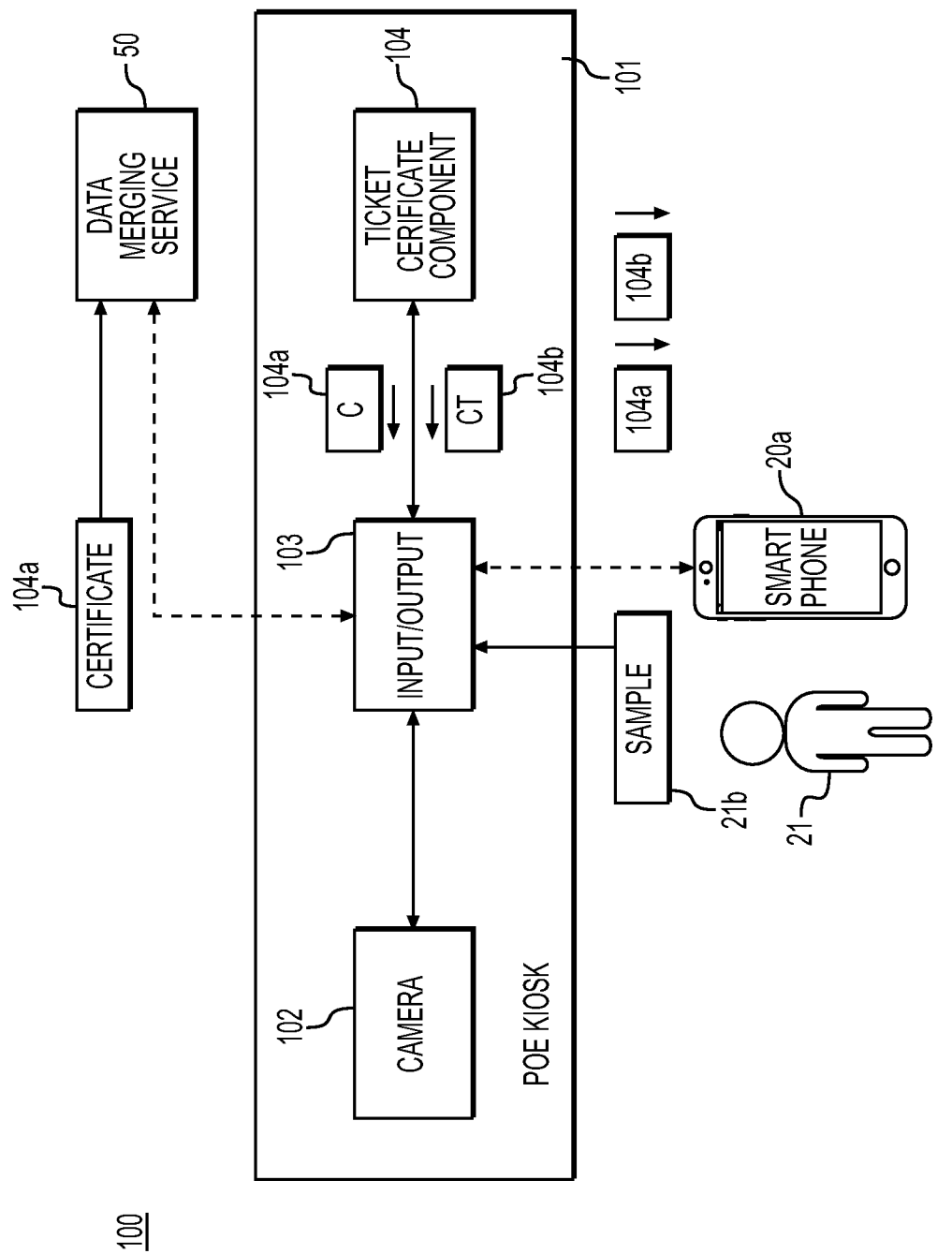
FIG. 4 illustrates an example implementation of components of the Health Status
Systems of FIGS. 1 and 2.

In an embodiment, an HSS may be implemented in part at a point of entry (POE) kiosk for a specific venue such as an airport, a stadium, a theatre, or an office building. FIG. 4 shows HSS 100 implemented at POE kiosk 101. The kiosk 101 includes camera 102, input and test device 103, and certification component 104. In an aspect, user 21 accesses test device 103 to access a sample collection instrument such as a swab (packaged in a sanitary container), uses the swab to collect a sample, and then inserts the swab in a collection por, at which time, the test device 103 reads and analyzes the collected and submitted sample. After analysis is complete, the test device 103 notifies the user 21 through a display that the test result in negative (good) or positive (not good). For negative test results, the test device 103 communicates the results to the certification component 104. The certification component 104 generates a certificate 104a, which the user may combine with an existing ticket to allow access to the venue associated with the POE kiosk 101. Alternately, such as when the user 21 does not have an existing ticket, the certification component 104 may generate a certified ticket 104b that may be used to access the venue. Generating the certificate 104a may require payment of a fee. Generating a certified ticket 104b would also include the base cost of ticket. In some aspects, the certificate 104a may not require payment of a separate fee.

Either the certificate 104a or the certified ticket 104b could be printed or could be provided to the user's smart phone 20a. The camera 102 my record the sample submission and provide a still image of the user 21 on the certificate 104a or the certified ticket 104b. The certificate 104a and the certified ticket 104b may come with a time to live, after which the user may not be able to access the venue.

In an aspect, the HSS 100 may provide a certificate 104a to a data merging service 50, where the certificate 104 may be used, within its time to live, to access other activities at the venue. However, a likely implementation is that the assigned time to live would expire at the end of the specific event at the venue to which the user 21 requests access, or shortly thereafter.

Figure 5:
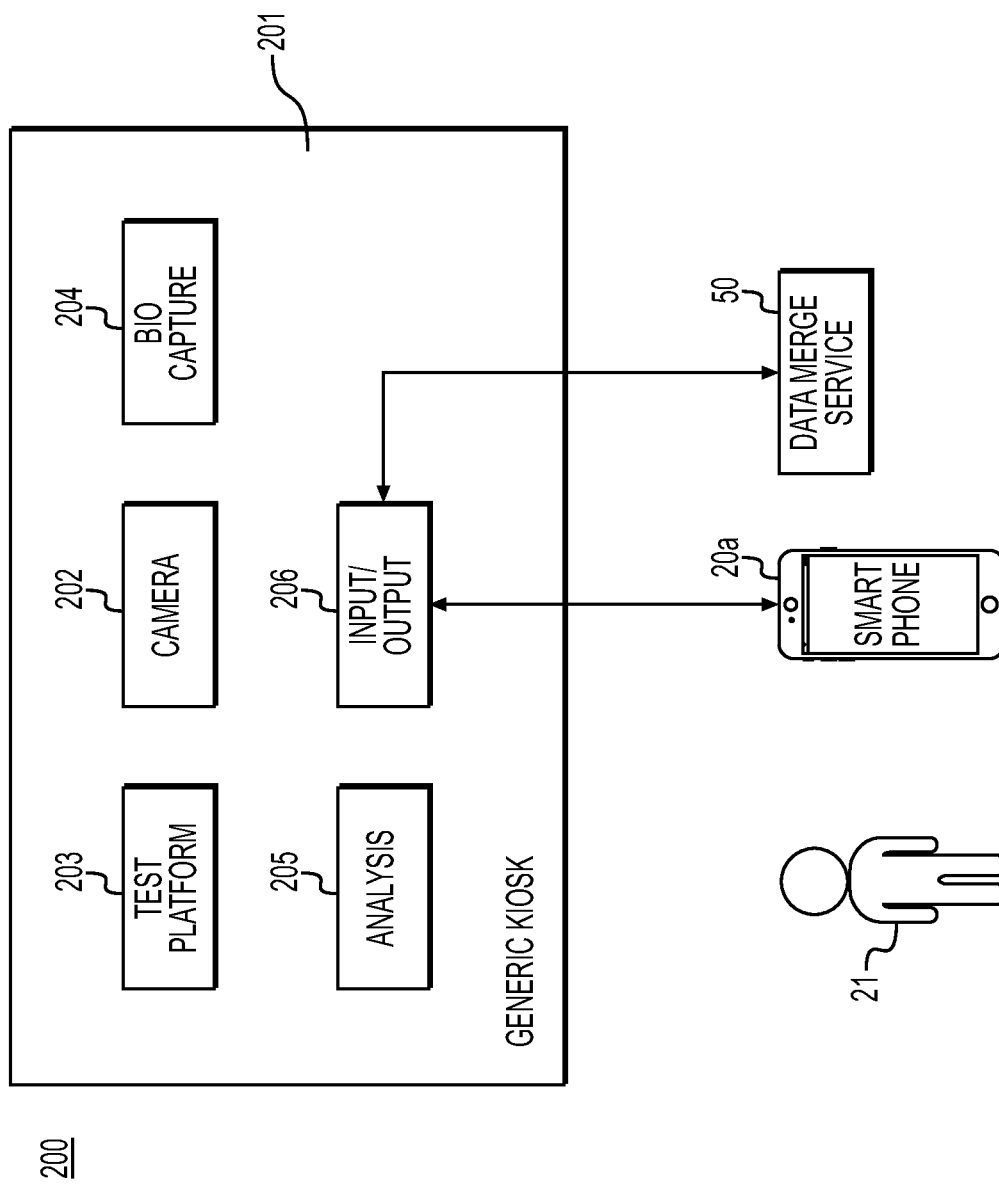
FIG. 5 illustrates another example implementation of the Health Status Systems of FIGS. 1 and 2.

FIG. 5 illustrates a generic kiosk 201 that may be implemented as a component of HSS system 200. The kiosk 201 may be installed at a point of sale of test kits (see, for example test kit 300 of FIG. 6) or supplies such as swabs that are used to collect a sample, such as at a pharmacy. The kiosk 201 may be installed at public access facilities such as museums for which separate access tickets are not required, at shopping malls, for example, and at indoor and outdoor facilities that generally are open to the public. The kiosk 201 may be installed at transportation hubs such as airports, train stations, or mass transit entry points. The kiosk 201 may be installed at a multi-tenant building or a hotel, resort, or casino.

The kiosk 201 includes camera 202, test platform 203, biometrics capture component 204, sample analyzer 205 and digital data input/output 206. The kiosk 201 may be connected to an AC power source, may be battery powered, or may be solar powered, or may be powered by a combination of the foregoing such that upon a loss of AC power, the kiosk 201 may continue to operate. The input/output 206 may include a visual display section or user interface and a mechanism such as a key pad or qwerty keyboard for data entry. The input/output 206 may connect to a wired or wireless data input to receive data from and send data to, for example, smart phone 20a and data merge service 50. To collect and analyze a sample, the kiosk 201 may provide in a user interface of the input/output 206, a menu of test options and instructions for completing a desired test. Note that the kiosk 201 may be configured to acquire and analyze samples for a variety of illnesses. The desired test may be preceded by collection of image data of the user 21 through camera 202, where the image data may be digital still frame images, or video. If implemented, the test also may be preceded by collection of biometric information from the user 21, such as thumbprints. In a test operation, the kiosk 201 provides, through test platform 203, a sample collection device (e.g., a swab). After sample collection, the sample collection device is placed in a receptacle of the test platform 203 and the sample is read. The sample results may be transmitted to the analysis competent (analyzer) 205, where the reading is determined to indicate a negative or positive value, and/or, in some embodiments, to provide a quantitative value. The determined value is provided to the input/output 206, where the results may be displayed in the user-readable window or interface. The determined value is time-stamped, and data describing and identifying the kiosk, the sample obtained, the user 21, and the test performed are added to the time-stamped value to provide a certified test result that then may be transmitted to the user's smart phone 20a and/or the data merge service 50. In an event where the test result is not or cannot be certified, the test result may be provided to a certificate service (not shown in FIG. 5).

The herein disclosed embodiments of an HSS provide a significant technical advance over existing sample regimes and modalities at least in part because of incorporation of verifiable at-home testing afforded to users such as user 21 of FIG. 2, with the at-home testing capable of producing an authenticated and certified test result that may be employed to gain safe and secure access to a variety of venues over a defined period. For example, a single at-home test may allow access to air travel as well as theaters, sporting events, and other public events that may draw a large number of people.

Figure 6:
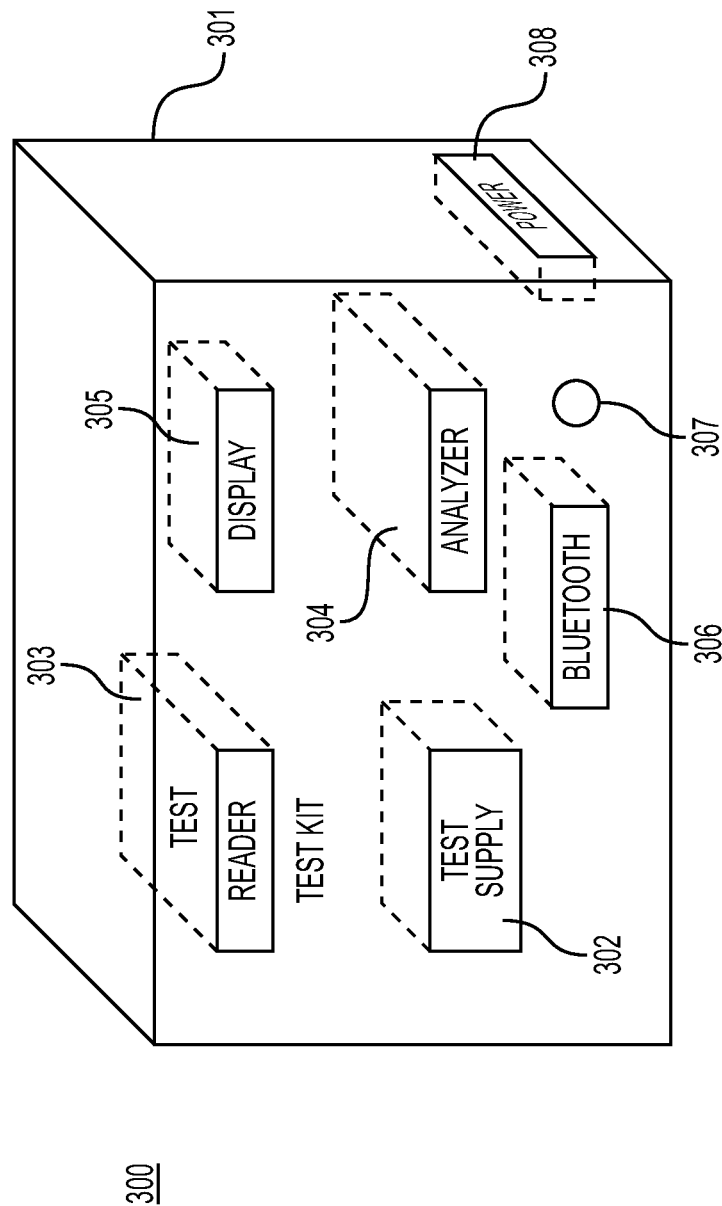
FIG. 6 illustrates an example test kit operable with the Health Status Systems of FIGS. 1 and 2.

One aspect of an HSS is an at-home test kit, namely the rapid test platform 30 of FIG. 2. FIG. 6 illustrates an embodiment of an at-home test kit 301. The at-home test kit 301 may be a standalone device or may operate in cooperation with an application, such as application 22 of FIG. 2 installed on a smart device such as smart phone 20a of FIG. 2. In FIG. 6, at-home test kit 301, as part of HSS 300, is seen to include test sample acquisition supply 302, which may contain a swab or other sampling device. The kit 301 further includes a test reader 303 that reads the collected sample and analyzer 304 that determines a value of the read sample results. For example, the analyzer 304 may determine a read sample indicates presence or absence of a virus, and/or may provide a quantitative value. A display 305 may present the sample result as determined by the analyzer 304 in a form and format that may be understood by a user. The display 305 also may display instructions for operation of the kit 301. The instructions may be provided by internal components of the kit 301 or by application 22 in communication with the test kit using wired connection 307 or wireless Bluetooth connection 306. Finally, the kit 301 may include a battery power supply 308 with exchangeable batteries.

In an embodiment, the kit 301 is a one-time-use device. After a sample is received, analyzed and reported, the kit 301 may be incapable of any further function. In another embodiment, the kit 301 may be refurbished and reused, or may be employed by the same user 21 for one or more additional tests, including tests other than previously executed tests; that is, the kit 301 may be used for multiple, different modalities. In this embodiment, the kit 301 may employ a counter, and a current count may be included with a reported test. The number of tests that the kit 301 may execute may be limited, and the kit 301 may be unusable once the counter has reached a predetermined count.

In addition to the embodiments shown in FIGS. 1-6, as described herein, an HSS may be implemented in part at a medical clinic, facility, or hospital. For example, sample collection, analysis, and reporting may be performed at or initiated at a medical clinic. Further functions of the HSS may include those executed by the remaining components of FIG. 2, for example. Thus, a medical clinic may communicate test results to certification component 4 and data merge component 5. Such communications may be encrypted to ensure validity and authenticity of the reported test result, to prevent hacking, and to ensure compliance with all requirements in place to allow venue access.

Figure 7A:
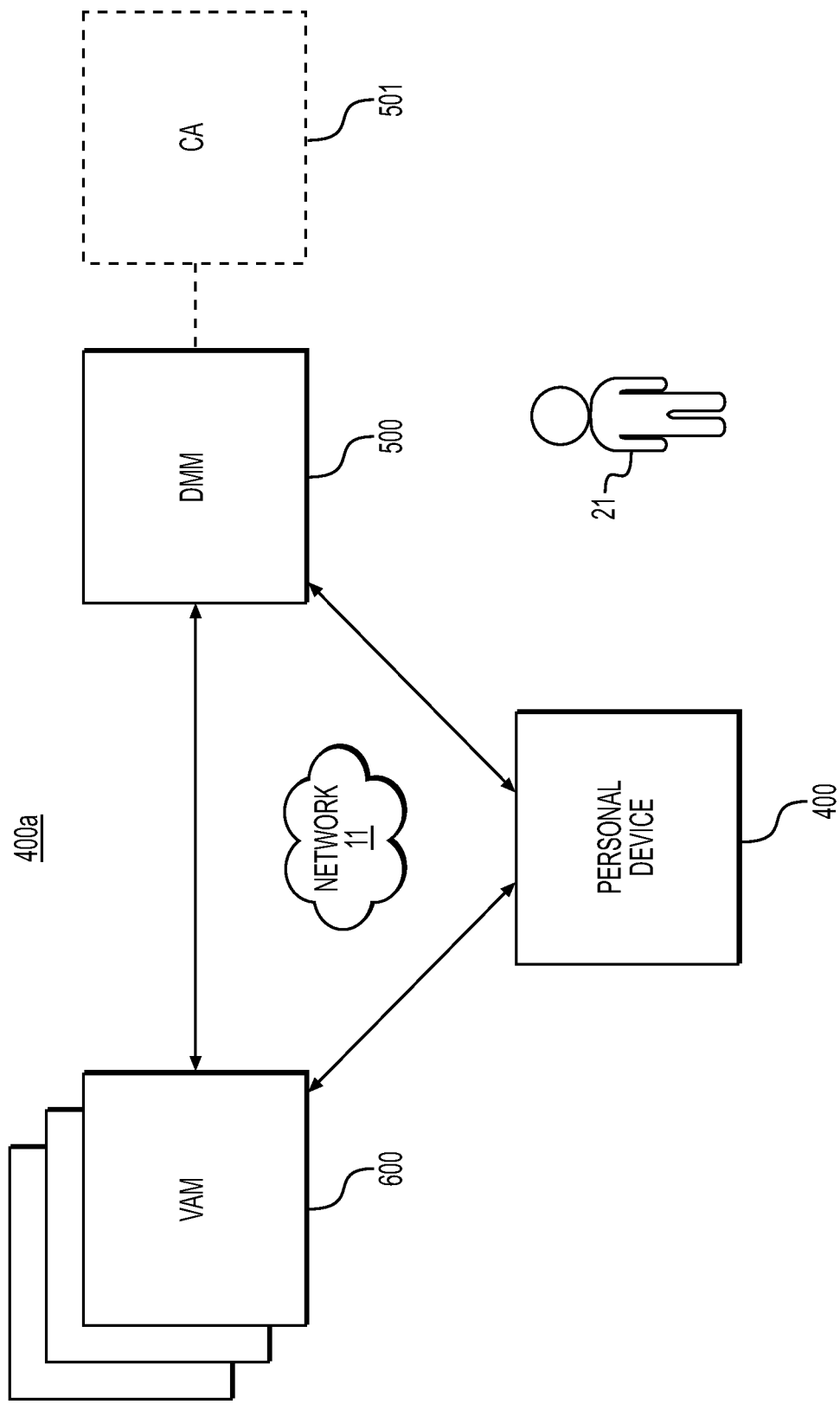
FIGS. 7A-7C illustrate another example Health Status System, and components thereof.

FIG. 7A is a block diagram of entities in Health Status System 400a. The entities include smart personal device (PD) 400 under control of user 21, data merging module (DMM) 500, and one or more venue access modules (VAM) 600. Optionally, the system 400a may include a separate certificate module 501. Otherwise, the certificate module 501 may be incorporated in the DMM 500. The entities shown in FIG. 7A may communicate over network 11.

Figure 7B:
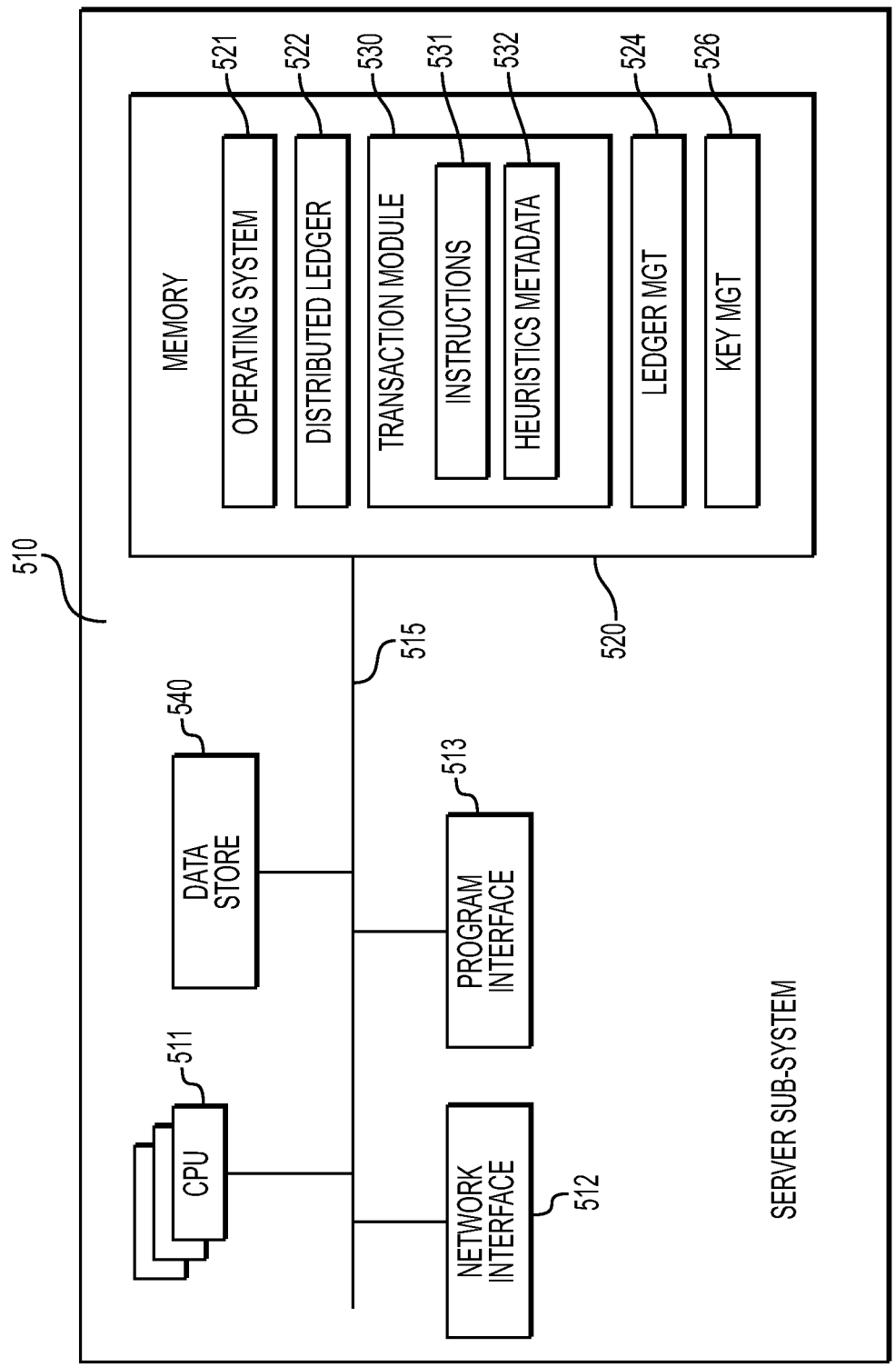

FIG. 7B shows illustrates portions of the DMM 500 in more detail. DMM 500 includes server sub-system 510. Server sub-system 510 in turn includes one or more CPUs 511, network interface 512, program interface 513, and memory 520. Memory 520 is a non-transitory computer-readable memory. Memory 520 includes server operating system (OS) 521 and transaction module 530. Transaction module 530 includes machine instructions 531, which may be loaded from non-transitory computer-readable storage medium (i.e., data store) 540, and heuristics and metadata 532. The CPUs 511, network interface 512, program interface 513, memory 520, and data store 540 communicate over system bus 515. The operating system 521 includes procedures for handling various basic system services and for performing hardware dependent tasks. The transaction module 530 manages transactions between entities in the HSS 400a. For example, the transaction module 530 may transmit a key request to a network node within a cluster of network nodes (i.e., venue access components in VAM 600) that are configured to maintain a distributed ledger. The transaction module 530 receives a key in response to transmitting the key request, and synthesizes transaction data with the key. The transaction module 530 transmits the transaction data to another entity. In an aspect, the transaction module 530 is configured to perform the method 800 shown in FIG. 8. The transaction module 530 receives transaction data, transmits a validation request to determine whether the key utilized to synthesize the transaction data is valid, receives a validation response, and utilizes the transaction data to complete a transaction if the validation response indicates that the key is valid. The transaction module 530 is configured to perform the method 800 shown in FIG. 8. To that end, the transaction module 530 includes machine instructions 531, and heuristics and metadata 532.

The memory 520 and/or the data store 540 also stores programs, modules and data structures to enable a distributed ledger 522, a ledger management module 524, and a key management module 526. The distributed ledger 522 may be distributed over various network nodes. In an aspect, each network node stores a local copy of the distributed ledger 522. The distributed ledger 522 may store information regarding transactions between different entities in the HSS 400a. In an aspect, the distributed ledger 522 stores a batch of transactions in a block. In an aspect, each block is timestamped. The ledger management module 524 manages the distributed ledger 522. For example, the ledger management module 524 functions to ensure that the local copy of the distributed ledger 522 is synchronized with the local copy of the distributed ledger 522 at other network nodes. In an aspect, the ledger management module 524 participates in consensus protocols associated with the distributed ledger 522. For example, the ledger management module 524 may propose new blocks for the distributed ledger 522 and/or votes on block proposals received from other network nodes. To that end, the ledger management module 524 includes machine instructions, and heuristics, and metadata. The key management module 526 receives a key request from an entity, determines whether the key request is valid, synthesizes a key if the key request is valid, transmits the key to the entity, and stores the key in the distributed ledger 522. The key management module 526 determines whether the key request is valid by determining whether one or more validation criterion stored in the distributed ledger 522 is satisfied. For example, the key management module 526 may execute the method 900 shown in FIG. 9. The key management module 526 receives a validation request from an entity, accesses the distributed ledger 522 to determine whether the key utilized to synthesize the transaction data is valid, and transmits a validation response that indicates the validity status of the key to the entity. The key management module 526 performs the method 900 shown in FIG. 9. To that end, the key management module 526 includes machine instructions, heuristics, and metadata.

Figure 7C:
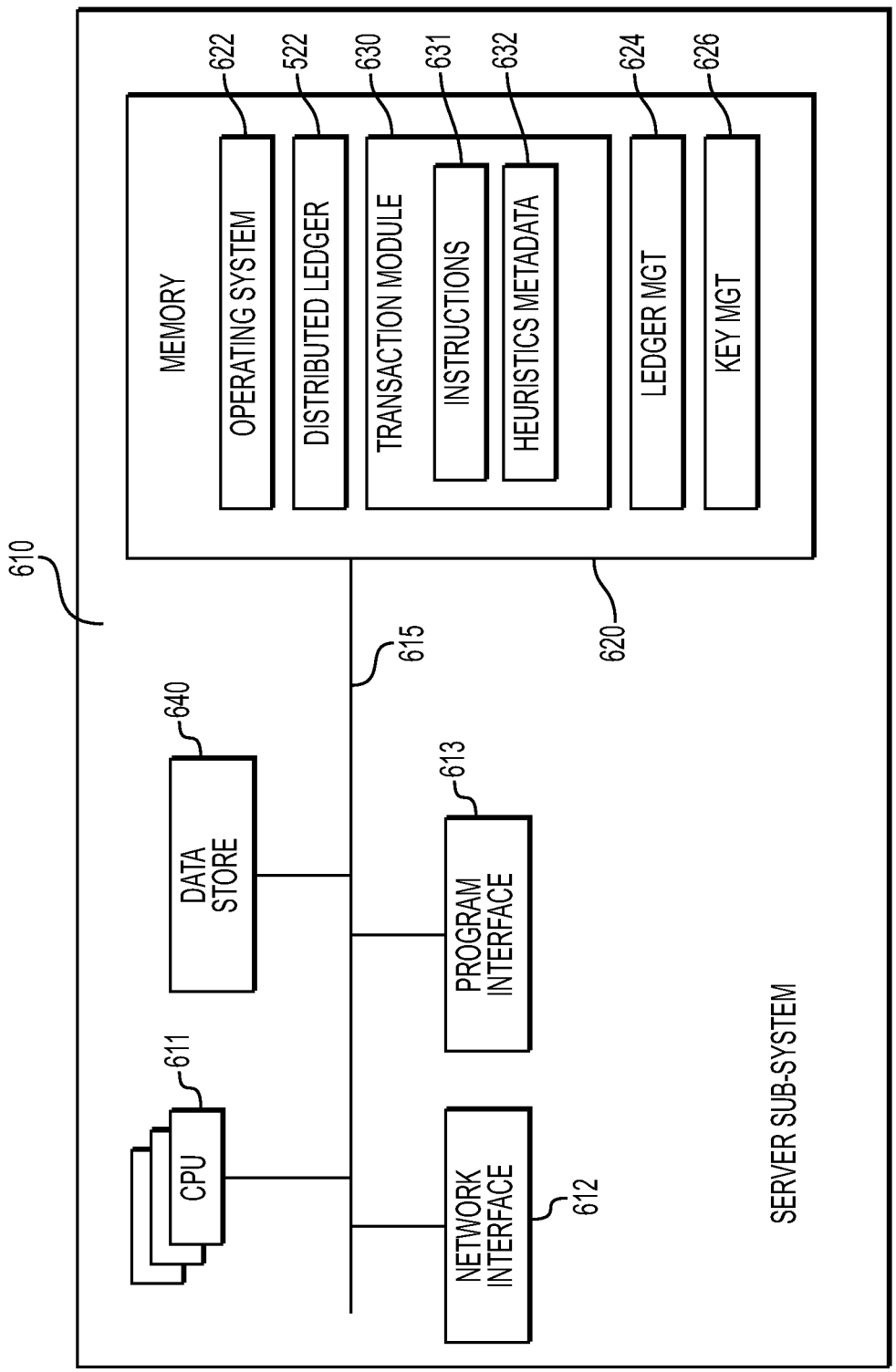

FIG. 7C illustrates the VAM 600 in more detail. In an embodiment, the VAM 600 may be enabled at various modules associated with and/or included in a network node of the network 11. The VAM 600 includes server sub-system 610, which in turn includes one or more processing units (CPUs) 611, network interface 612, program interface 613, a memory 620, data store 640, and communication bus 615. The memory 620 and/or the data store 640 stores programs, modules and data structures, or a subset thereof to include an operating system (OS) 622, a distributed ledger 522, a ledger management module 624, and a key management module 626. The distributed ledger 522, the ledger management module 624 and the key management module 626 may be similar to corresponding components of the DMM 500 shown in FIG. 7B. The operating system 622 includes procedures for handling various basic system services and for performing hardware dependent tasks. The distributed ledger 522 may be distributed over various network nodes. In an aspect, each network node stores a local copy of the distributed ledger 522. The distributed ledger 522 may store information regarding transactions between different entities in the HSS 400a. In an aspect, the distributed ledger 522 stores a batch of transactions in a block. In an aspect, each block is timestamped. The ledger management module 624 manages the distributed ledger 522. For example, the ledger management module 624 functions to ensure that the local copy of the distributed ledger 522 is synchronized with the local copy of the distributed ledger 522 at other network nodes. In an aspect, the ledger management module 624 participates in consensus protocols associated with the distributed ledger 522. For example, the ledger management module 624 may propose new blocks for the distributed ledger 522 and/or votes on block proposals received from other network nodes. To that end, the ledger management module 624 includes machine instructions and heuristics and metadata. The key management module 626 receives a key request from an entity, determines whether the key request is valid, synthesizes a key if the key request is valid, transmits the key to the entity, and stores the key in the distributed ledger 522. The key management module 626 determines whether the key request is valid by determining whether one or more validation criterion stored in the distributed ledger 522 is satisfied. For example, the key management module 626 performs the method 900 shown in FIG. 9. The key management module 626 receives a validation request from an entity, accesses the distributed ledger 522 to determine whether the key utilized to synthesize the transaction data is valid, and transmits a validation response that indicates the validity status of the key to the entity. To that end, the key management module 626 includes instructions and/or logic 631, and heuristics and meta data 632.

Figure 7D:
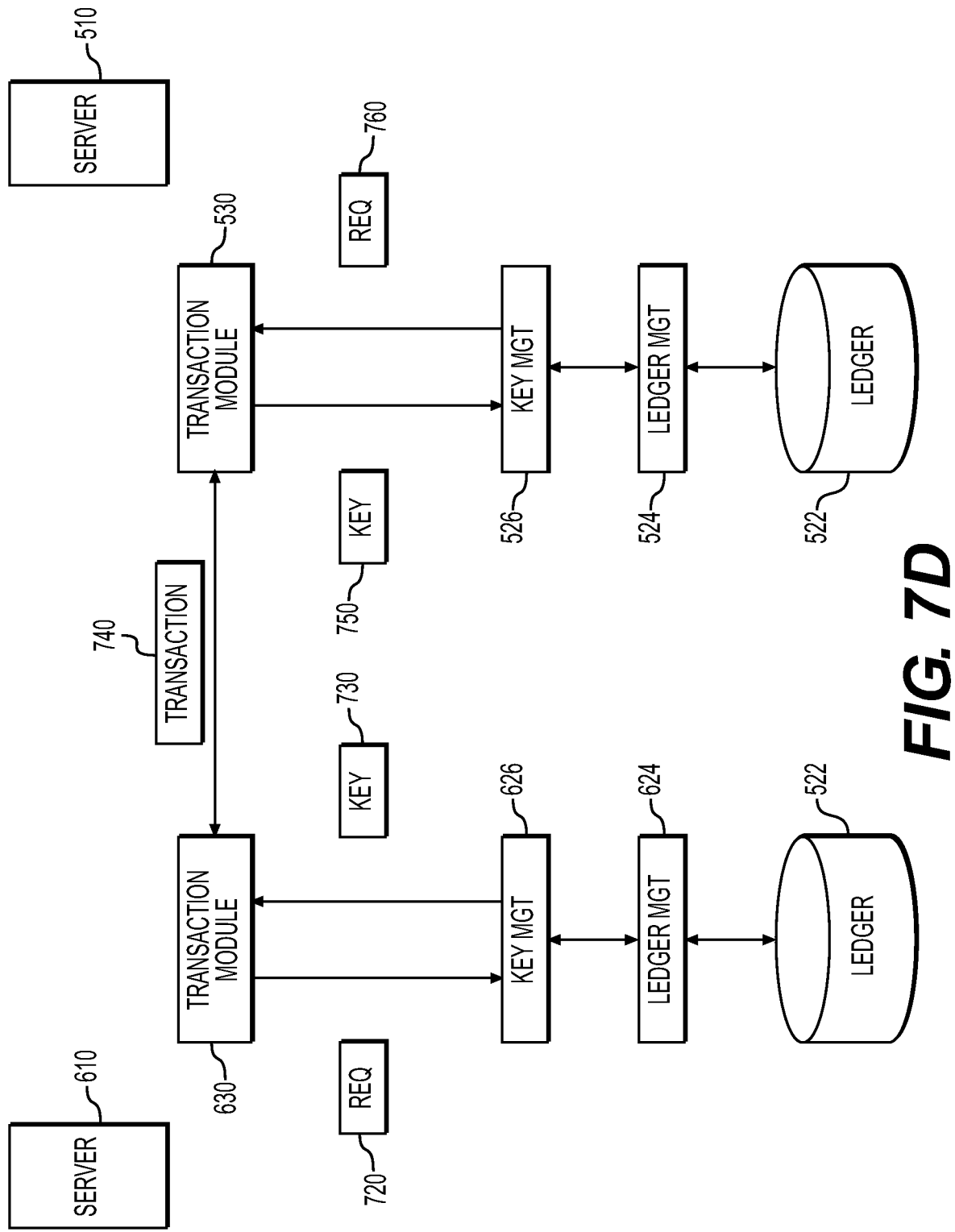
FIG. 7D illustrates an example transaction operation executable between components of the Health Status System of FIGS. 7A-7C.

FIG. 7D illustrates a transaction operation between entities in the system 400a of FIG. 7A. In operation, the servers 510, 610 enable secure transaction between or on behalf of entities in the HSS 400a of FIG. 7A. For example, the servers 610 and 510 may execute transactions on behalf of a venue and user 21, respectively. To this end, each server 510 and 610 implement a transaction module 530, 630. Thus, the transaction modules manage transactions between entities such as a venue and the smart personal device 400, and in an aspect, a transaction module may be associated with (e.g., owned by) one or more externally owned accounts that manage the transactions. In an example, a first externally owned account is controlled by user 21 while a second externally owned account is controlled by a venue or a venue's agent. As a result, the user 21 may have access to a private key that controls the externally owned account.

As FIG. 7A illustrates, the HSS 400a includes a cluster of network nodes (i.e., VAMs 600) connected by network 11.

The VAMs 600 cooperate with the DMM 500 to generate and maintain a distributed ledger 522. In an aspect, each VAM 600 stores a local copy of the distributed ledger 522, and DMM 500 stores a complete copy of the ledger 522. Thus, in FIG. 7D, servers 510 and 610 store a copy of the distributed ledger 522. In an aspect, the distributed ledger 522 stores (e.g., records) transactions (e.g., all the transactions) between the entities (venues) represented by the VAMs 600 and the entity (smart personal device) 400. The distributed ledger 522 also may store metadata associated with the entities.

The distributed ledger 522 further may store contract accounts that include programs with computer-executable instructions. In an aspect, the contract accounts are associated with respective contract codes. In an aspect, the contract accounts correspond to respective externally owned accounts. In such aspects, the contract accounts are controlled by their corresponding externally owned accounts. As such, the distributed ledger 522 supports externally owned accounts and contract accounts. In an aspect, the distributed ledger 522 implements a data structure that includes various blocks, with each block holding a batch of individual transactions and including a timestamp indicating block inclusion in the ledger 522. The blocks also may, but need not, include information linking a succeeding block to a previous block. For example, a succeeding block includes a hash of a previous block. When implemented in this fashion, the distributed ledger 522 is referred to as a blockchain.

Each server 510, 610 may include a ledger management module, and a key management module, as shown in FIG. 7D. The ledger management modules manage the distributed ledger 522. For example, the ledger management modules may propose new blocks for the distributed ledger 522 (each proposed block containing one or more transactions). The ledger management module further performs operations to ensure that the network node includes an updated copy of the distributed ledger 522. For example, a ledger management module of a first VAM 600 performs operations to ensure that the local copy of the distributed ledger 522 stored at a first VAM 600 is the same as the local copy of the distributed ledger 522 stored at a second VAM 600. Generally, the ledger management module serves as an interface for the distributed ledger 522. For example, the key management module may access the distributed ledger 522 by way of the key management module.

In operation, a transaction module of server 610 may initiate a transaction with the server 510. For example, the personal smart device 400 may communicate with a venue represented by VAM 600 to access that venue. That is, an externally owned account associated with a venue determines to initiate a transaction with an externally owned account associated with the user 21. To execute this transaction, the transaction module of server 610 first may query the distributed ledger 522 to determine if a certification transaction is stored therein that would satisfy access requirements for the venue. The distributed ledger 522 may contain the certification transaction but not the required key. Alternately, the distributed ledger 522 may contain both the key and the certification transaction. Alternately, the distributed ledger 522 could contain neither. Assuming only the key is not available, the server 610 may request the server 510 provide the required key. In response, the transaction module transmits a key request 720 to the key management module. The key request 720 may indicate that the VAM 600 has determined to complete one or more transactions with the smart personal device 400. In an aspect, the key request 720 is to occur between the VAM 600 and the smart personal device 400. In an aspect, the key request 720 indicates a requested transaction type (e.g., health certification (i.e., the key request 720 is for a health credential that the transaction module requires to complete the transaction(s)).

In an aspect, the key management module provides a key 730 in response to receiving the key request 720. In an aspect, the key management module determines whether the key request 720 is a valid request. In an aspect, the key management module accesses the distributed ledger 522 to determine whether the key request 720 satisfies one or more validation criterion. For example, the key management module may query the distributed ledger 522 to determine whether the VAM 600 and the smart personal device 400 are permitted to transact with each other. In another example, the key management module may query the distributed ledger 522 to determine whether the requested time duration, the requested number of transactions, and/or the requested transaction type are permitted. Other validation criteria also are possible. In yet another example, the key management module may query the distributed ledger 522 to determine whether the smart personal device 400 has provided a preference for transactions.

In an aspect, the key management module synthesizes the key 730. In an aspect, the key 730 may be a cryptographic key. In another aspect, the key 730 includes a session key, a pair of keys (e.g., a public key and a private key). In some examples, the pair of keys are asymmetric or a single shared key. For example, the key management module may employ a variety of symmetric-key algorithms, such as Data Encryption Standard (DES) and Advanced Encryption Standard (AES), to generate the key 730. Alternately, the key management module employs a variety of public-key algorithms, such as RSA, to generate the key 730. In an aspect, the key 730 includes a random number. In another aspect, the key 730 is the output of a hash function, where the hash function is a hash of the names of the entities, a time of day, and/or a random number. In another aspect, the key 730 includes a credential. In a further aspect, the first key management module may synthesize the key 730 by activating a contract account that is associated with an externally owned account associated with by the first transaction module. For example, the first key management module may execute instructions associated with the contract account. In this further aspect, the key request 720 may include a contract code for the contract account, and the first key management module employs the contract code to activate the contract account.

In an aspect, the key 730 is associated with a key identifier (ID) that identifies the key, and a validity period that indicates a time duration during which the key 730 is valid. The validity period may be equal to a requested time duration. However, if the requested time duration is greater than a threshold time duration, the validity period may be limited to the threshold time duration. In a further aspect, the key 730 may be associated with a validity number that indicates a number of transactions that can be completed with the key 730. The validity number may be equal to a requested number of transactions. However, if the requested number of transactions is greater than a threshold number of transactions, the validity number may be limited to the threshold number of transactions. In a still further aspect, the key 730 is associated with a validity type that indicates a transaction type that may be completed with the key 720. The validity type may be the same as a requested transaction type. However, if the requested transaction type includes transaction types that are not permitted, the transaction may not be permitted. In an embodiment, the threshold time duration, the threshold number of transactions, and/or the permitted transaction types are represented by one or more validation criterion stored in the distributed ledger 522.

The transaction module 630 may employ the key 730 to synthesize the transaction data 740. In an aspect, the transaction data 740 includes signed data, and the transaction module 630 employs the key 730 to generate a digital signature and to sign the transaction data. In an aspect, the transaction module 630 signs the transaction data 740 (e.g., a hash of the transaction data) with the key 730. A person of ordinary skill in the art will appreciate that the transaction module 630 may employ a variety of signing techniques to synthesize the signed data. For example, the transaction module 630 may employ a Digital Signature Algorithm (DSA) and/or Elliptic Curve Digital Signature Algorithm (ECDSA) to synthesize the signed data. In an aspect, the transaction data 740 includes encrypted data. In this aspect, the transaction module 630 employs the key 730 to encrypt the transaction data 740. Other signing and/or encrypting techniques also are possible. When signed and encrypted, the transaction module 630 transmits the transaction data 740.

The transaction module 530 receives the transaction data 740 and completes the transaction based on the transaction data 740. The transaction module 530 may determine whether the transaction data 740 is valid by, for example, determining whether the key 730 employed to synthesize the transaction data 740 is valid. As such, the transaction module 530 transmits a validation request 750 to the key management module 526. In an aspect, the validation request 750 includes the key 730 (e.g., when the transaction data 740 includes the key 730). In another aspect, the validation request 750 includes the key ID. In yet another aspect, the validation request 750 includes only the transaction data 740. The key management module 526 receives the validation request 750 and determines whether the key 730 employed to synthesize the transaction data 740 is valid by, for example, querying the distributed ledger 522 with the key 730 and/or the key ID. The second key management module 524 then transmits a validation response 760 to the transaction module 530. The validation response 760 indicates a validity status of the key 730. For example, the validation response 760 may indicate the validity period, the validity number, and/or the validity type associated with the key 730 are satisfied.

Based on the validation response 760, transaction module 530 employs the transaction data 740 to complete the transaction. For example, the transaction module 530 may complete the transaction if the validation response 760 indicates that the transaction data 740 was synthesized with a valid key (e.g., the key 730 is valid). In an aspect, the transaction module 530 may further require a current time is within the validity period indicated by the validation response 760, that a current transaction type associated with the transaction data 740 is the same as the validity type indicated by the validation response 760, that a transaction counter indicates the number of transactions completed with the key 730 is less than the validity number indicated by the validation response 760. Note that some transactions when completed may involve executing a smart contract, or completing a money transfer. Thus, in a further aspect, the transaction module 530 may access the distributed ledger 522 to determine whether the transaction is permitted. If the distributed ledger 522 indicates that the transaction is permitted, the second transaction module 530 completes the transaction.

In an embodiment, a transaction module may synthesize a digital wallet, which creates an externally owned account. For example, the transaction module may synthesize a digital wallet for user 21. The digital wallet may be implemented on smart personal device 400. The digital wallet allows user 21 to may online or other electronic purchases, and also provides user 21 with a convenient storage for certified access tickets, for example.

Figure 7E:
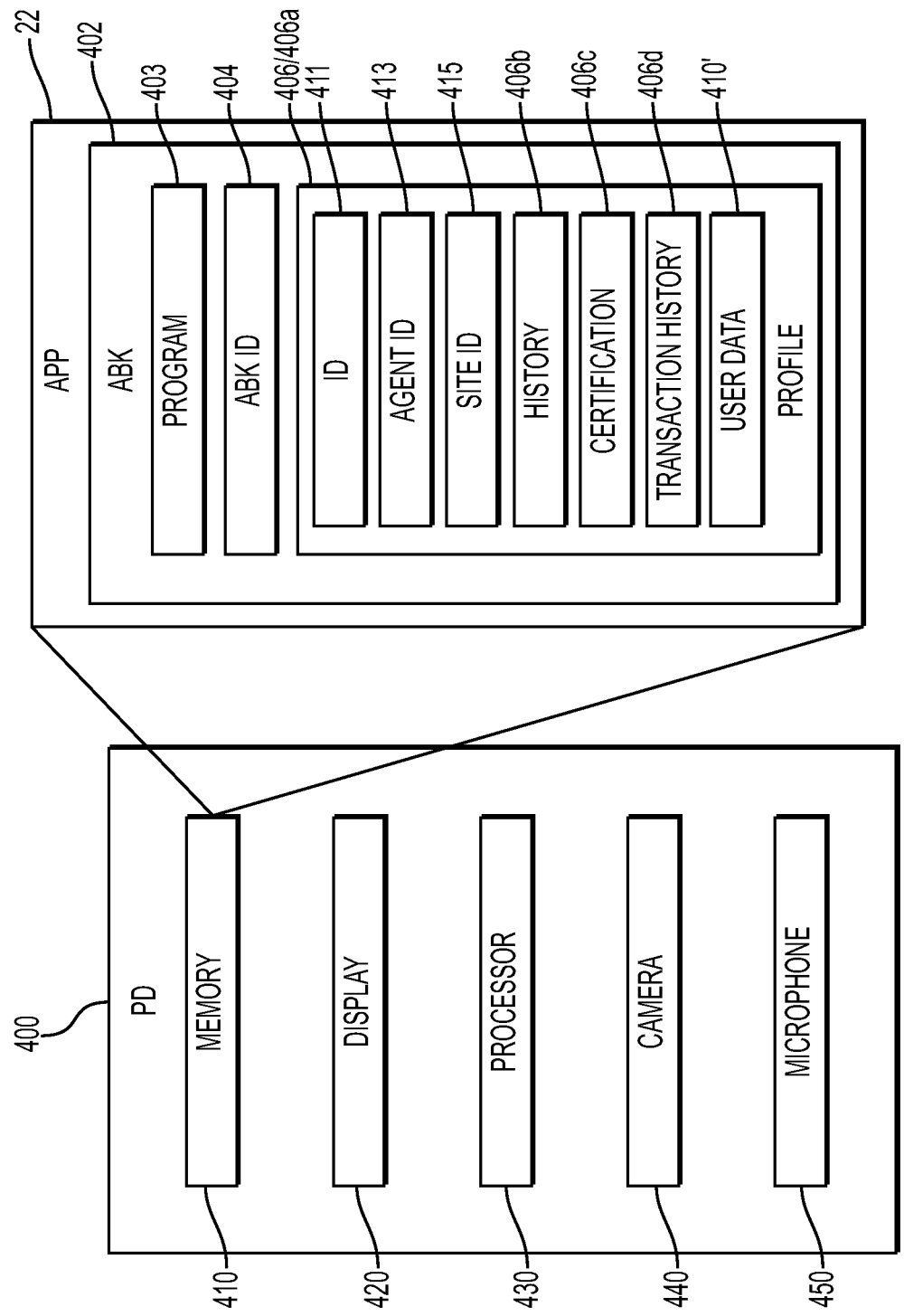
FIG. 7E illustrates an example Health Status System application as implemented on a user's smart device.

FIG. 7E illustrates an example of an application biometric key (ABK) component 402. The ABK 402 resides in memory 410 of the smart personal device (PD) 400 and cooperates with software and hardware components of the PD 400, including display 420, processor 430, camera 440, and microphone 450. The ABK 402 may be implemented as part of application 22 of FIG. 1, and may be acquired and activated with acquisition and activation of application 22. However, application 22 may be operated without activation of ABK 402. Alternately, ABK 402 may be acquired and activated separate from application 22, but will cooperate with application 22. In another aspect, the functions of the ABK 402 may be implemented in a hardware device that may be integrated into the PD 400. The ABK 402 may be provided with a unique ABK ID 404 and one or more profiles 406. The ABK ID 404 may include a public section and a private section, each of which may be used for identification and authentication. In an embodiment, the ABK ID 404 may be stored in a read-only format. The ABK ID 404 may be employed as an identifying feature of the ABK 402 and distinguishes between ABKs 402 in the DMM 500 or VAM 600. The ABK 402 may include a program of instructions 403 by which the functions of the ABK 402 are executed.

The profile 406 may, in addition to containing biometric data 406*a*, include a profile history 406*b*, a profile certification 406*c*, a transaction history 406*d*, and other data 410'. Profile biometric data 406*a*, for example, includes data representing physical and/or behavioral information that can uniquely identify the user 21. The ABK 402 may operate to cause storage of multiple biometric profiles 406, each profile 406 for a different type of biometric data. In an embodiment, a biometric profile 406 may include either or both digital data and analog data. The biometric profile 406 may include a jpeg image. Biometric data 406*a* may be transformed by a mathematical operation, algorithm, or hash that represents the complete biometric information (e.g., a complete fingerprint scan, a complete retina scan). In an aspect, a mathematical hash may be a "one-way" operation such that there is no practical way to re-compute or recover the complete biometric information from the biometric profile 406. This both reduces the amount of data to be stored and protects the user's personal biometric information. In an aspect, the biometric profile 406 is further protected by encoding using an encoding key and/or algorithm that is stored with the biometric data 406*a*. Then, for authentication, both the biometric data 406*a* and the encoding key and/or algorithm are passed to the DMM 500/VAM 600.

In an embodiment, the ABK 402 operates to cause storage of a picture profile that includes one or more jpeg or analog images of the user 21. In a picture authentication operation, the image stored in the ABK 402 may be transmitted to a display at the point of entry of a venue to allow an administrator (e.g., a clerk or security guard) to confirm or reject the identity of the user 21 requesting venue access. In another embodiment, an image of the user 21 may be captured at the point of entry and is compared to the picture profile by an automated image analysis mechanism of the application 22 or an independent device associated with the point of entry. In a point of entry at, for example a hotel, casino, or restaurant, a host could greet the user 21 and allow entry based on recognition of the user's picture profile. The DMM 500 may receive the encoded biometric data 406*a* from the smart personal device 400 and may use the biometric data 406*a* as part of a certification process.

In an embodiment, the ABK 402 may automatically transmit encoded biometric data 406*a* to the DMM 500 when, for example, the user 21 selects this option in the application 22, and when the user 21 applies for access to a venue. In an embodiment, some biometric data 406*a* may be acquired by operation of the ABK 402 during a trusted initialization process that is administered by a trusted agent. In an embodiment, once initial biometric data 406*a* have been stored by operation of the ABK 402, the user 21 may add information through operation of the ABK 402 without a trusted agent through self-authentication. For example, an ABK 402 that has an associated stored biometric profile 406 may be unlocked by providing a matching biometric input. Once unlocked, the user 21 may add or remove additional profiles 406, credit card data, personal information, and other information through operation of the ABK 402. For example, in one embodiment, a user who has unlocked the ABK 402 may store additional biometric information (such as fingerprint information in addition to an existing retina scan).

The profile history 406*b* includes an ID field 411, an agent ID field 413, and a site ID field 415. The profile history 406*b* relates to the specific hardware, trusted agent, and site used at the time the profile data 406*a* were created and stored by operation of the ABK 402. In an aspect, each profile 406 stores its specific profile history 406*a* along with the biometric data 406*a* and other profile data. The profile history 406*b* can be recalled for auditing purposes at a later time to ensure the credibility of the stored data. In an embodiment, transaction history 406*d* also may be stored to a user data segment of the PD memory 410. Here, the ABK 402 stores information associated with any transactions made with the ABK 402, such as the venue name, date of access, and purchase amount.

The ABK 402 also may include programming to implement a biometric reader through cooperation with hardware and software components of the PD 400. For example, fingerprints, retina scans, and image may be captured through employment of an interactive display screen/interface 420 and camera 440, of the PD 400, as appropriate.

Figure 8:
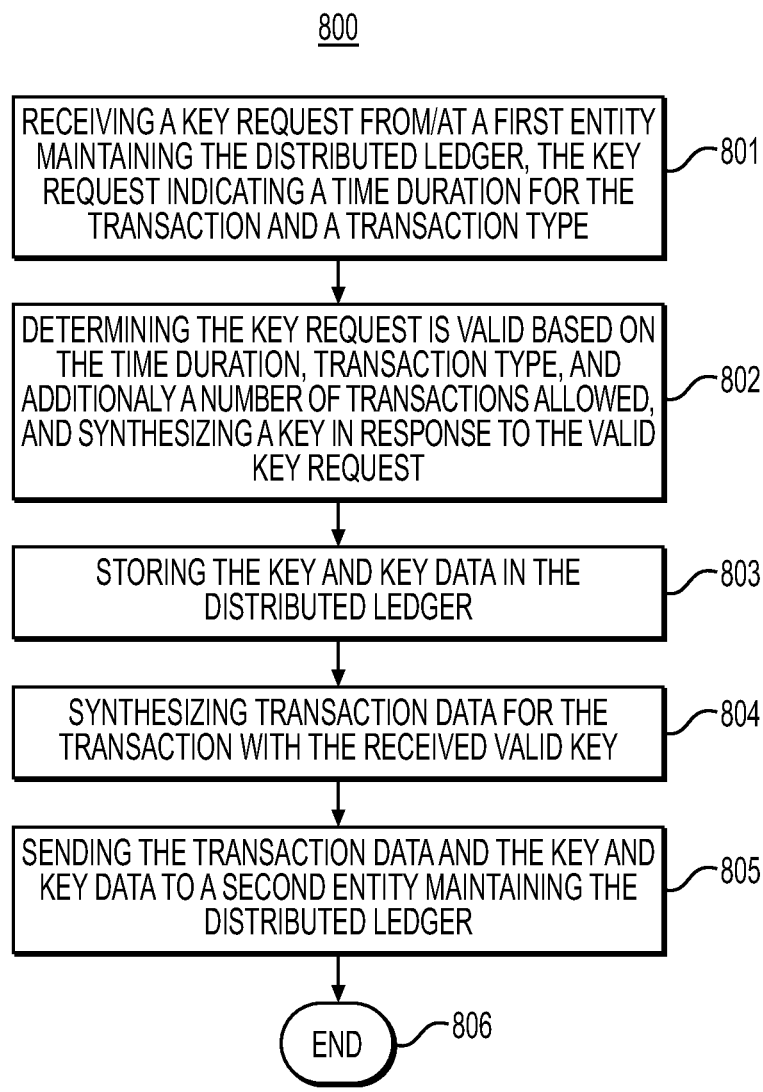
FIGS. 8 and 9 are flowcharts illustrating example operations of the Health Status System of FIGS. 7A-7C, and components thereof.

FIG. 8 is a flowchart illustrating an example operation 800 of components shown in FIGS. 7A-7E. For example, operation 800, as illustrated may be performed by either the DMM 500 or the VAM 600. Operation 800 begins in block 801 when a first entity, such as the VAM 600, receives a key request. The key request may be associated with an operation to be executed at the first entity, such as approving or certifying a transaction that involves access to a venue associated with the VAM 600. For example, the user 21, operating PD 400, may attempt to purchase a concert ticket for a venue associated with the VAM 600. For this transaction (purchase a ticket) to be approved, the user may be required to supply, or have supplied on behalf of the user 21, the user's health status. Note that if the concert is well after the purchase date (as might be normal), the HSS 10 may operate to require the user 21 to supply, or have supplied, a health certificate within a defined time window, such as 24 hours, before the concert date/time. However, for ease of illustration, the operation 800 will be further described assuming the certification and ticket purchase are contemporaneous. In this situation, the distributed ledger 522 may contain a block storing the user certification and other data necessary to grant access to the concert venue. (Note that any VAM 600 or the DMM 500 may propose a block for addition to the distributed ledger 522.) Thus, the first entity proceeds with block 802 to determine if the key request is valid. Validity may be based on one or more criteria including is the key request valid based on a predetermined time duration value, a number of times the key has been used compared to an allowed use number (note that a key may, in some embodiments, be used only once), the transaction type (e.g., purchase a ticket), and other validity criteria. When the key request is determined to be valid, the first entity synthesizes a key as part of the operation of block 802. In block 803, the first entity stores the key and any associated key data (e.g., key ID) in the distributed ledger 522, making the key accessible to any entity having access to the distributed ledger 522. Using the synthesized key, the first entity synthesizes (signs) the transaction, block 804. In block 805, the first entity sends the transaction, key, and key ID to the second entity. Operation 800 then ends, block 806.

Figure 9:
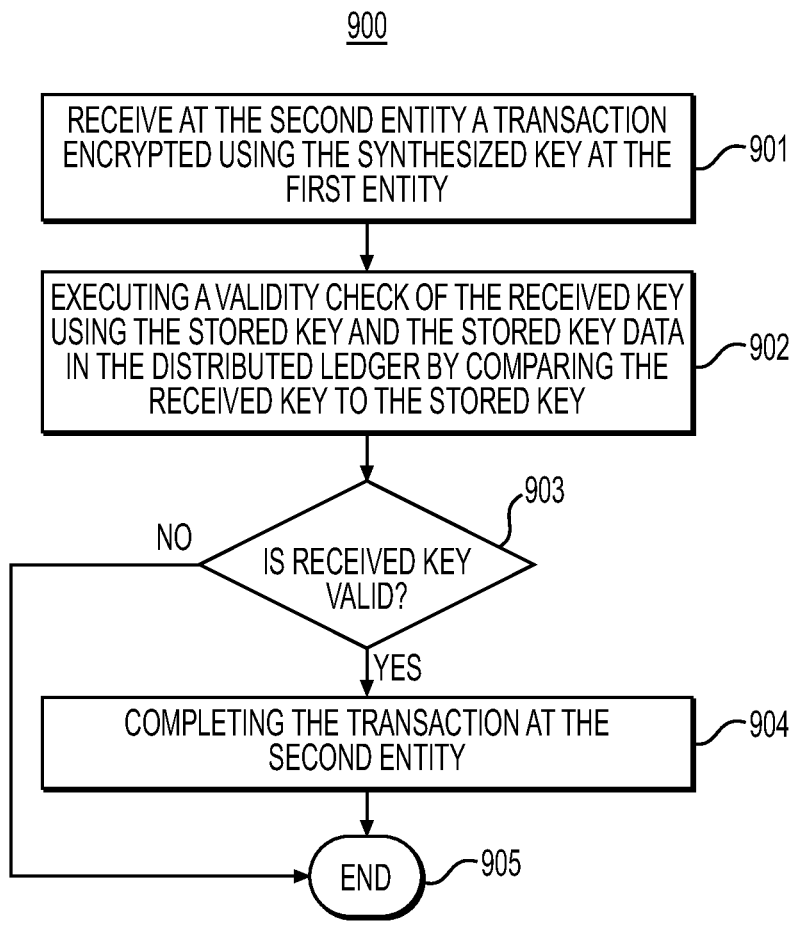

FIG. 9 is a flowchart illustrating another example operation of the components shown in FIGS. 7A-7E. For example, operation 900, as illustrated may be performed by either the DMM 500 or the VAM 600. Operation 900 begins in block 901 after receipt of the signed transaction sent in block 805 of FIG. 8. In block 902, the second entity executes a validity check of the key received with the transaction in block 901 by retrieving the key from the ledger 522 and comparing the retrieve key and the received key. In block 903, the second entity determines whether or not the received key is valid. If in block 903, the key is determined to be valid, operation 900 moves to block 904 and the second entity completes the transaction. If the key is not valid, or following block 904, operation 900 moves to block 905 and ends.

Following are example operating scenarios, and corresponding method steps, in which an HSS as disclosed herein (see, e.g., FIGS. 1-6) may be employed to enhance security and safety at a venue while ensuring the privacy of attendee data.

User 21 plans to take an airplane trip and the airline requires Sars-Cov-2 testing within 24 hours of boarding the flight. In step A, user 21 creates an account at the HSS 10 and receives an account ID. In step B, within 24 hours of boarding, the user 21 acquires a home Sars-Cov-2 test kit (e.g., kit 301 of FIG. 6). The test kit 301 comes with a unique test ID and is connected to the user's smart phone 20*a*. In step C, the user 21 performs the home test and receives a test result on smart phone 20*a*. In step D, using application 22 on smart phone 20*a*, the user 21 forwards the test result along with an attestation that these results are from a test that the user 21 self-performed, to the certificate service 40. In step E, the user 21 signs into an airline website to acquire a boarding pass. In step F, the user 21 receives a message from the airline system prompting the user 21 to provide a Sars-Cov2-test result before a boarding pass is issued. In step G, the user 21 enters the HSS account ID. In an aspect, the user 21 could provide the password to the HSS account to the airline, enabling the airline to provide valid credentials to the HSS 10 (the DMS 50) for retrieval of the test certification; alternately, the user could wait to be contacted from the HSS 10 to authorize release of the user's health certificate to the airline. Following completion of step G, the HSS 10 provides a test certification to the airline that the user 21 has had a negative test result within 24 hours prior to the boarding time.

User 21 wants to order an UBER driver and the driver requires a negative Flu A/B test within the prior 24 hours. In step A1, if user 21 already has an HSP account, the user 21 simply takes the home test and submit the results to the HSS 10. In step B1, an Uber application on smart phone 20*a* asks the user 21 to provide a health status certification prior to ordering an UBER driver. In step C1, user 21 enters the HSSP account ID. In step D1, Uber contacts the HSS 10 for health status verification. In step E1, the HSS notifies user 21 that Uber has requested their health status and the user authorizes the release of the user's health status to UBER. In step F1, UBER receives the health status and schedules the driver.

User 21 works at a meat-packing plant and must periodically update the HSS account with valid test results, as required by the company. In step A2, Company has the user's HSS account ID in the company's personnel records and checks at regular intervals that the employee is actively getting tested. Alternately, Company provides a regular testing facility on site and mandates that its personnel get tested there. In step B2, user 21 employs the HSS account ID for access to other venues by proving the user 21 are disease free and to maintain the proof.

The preceding disclosure refers to flowcharts and accompanying descriptions to illustrate the embodiments represented in FIGS. 7D, 8, and 9. The disclosed devices, components, and systems contemplate using or implementing any suitable technique for performing the steps illustrated. Thus, FIGS. 7D, 8, and 9 are for illustration purposes only and the described or similar steps may be performed at any appropriate time, including concurrently, individually, or in combination. In addition, many of the steps in the flow chart may take place simultaneously and/or in different orders than as shown and described. Moreover, the disclosed systems may use processes and methods with additional, fewer, and/or different steps.

Embodiments disclosed herein can be implemented in digital electronic circuitry, or in computer software, firmware, or hardware, including the herein disclosed structures and their equivalents. Some embodiments can be implemented as one or more computer programs; i.e., one or more modules of computer program instructions, encoded on computer storage medium for execution by one or more processors. A computer storage medium can be, or can be included in, a computer-readable storage device, a computer-readable storage substrate, or a random or serial access memory. The computer storage medium can also be, or can be included in, one or more separate physical components or media such as multiple CDs, disks, or other storage devices. The computer readable storage medium does not include a transitory signal.

The herein disclosed methods can be implemented as operations performed by a processor on data stored on one or more computer-readable storage devices or received from other sources.

A computer program (also known as a program, module, engine, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

We claim:

1. A health status method executed by a processor, comprising:
   receiving from a test system, by the processor:
      a representation of biological sample data of a human sample collected from a human user and analyzed by the test system for an indication of a presence of an infectious disease, and
      identification information identifying the user, the biological sample data comprising:
         the indication of the presence of the infectious disease;
         a time and date of sample collection of the biological sample; and
         an identification of the test system, and
      the information identifying the identity of the user comprising:
         an attestation of the identification of the user recorded in conjunction with collecting the biological sample of the user,
   registering and storing the biological sample data in a central storage;
   associating the attestation of the user with the biological sample of the user;
   generating a certificate of association between the attestation of the user and the biological sample of the user, comprising:
      analyzing the attestation of the user,
      based on the analysis, verifying that the collected biological sample was obtained from the identified user, and
      assigning a time to live for the certificate;
   receiving from a venue, an access request for the user to access the venue;
   determining the access request is for a time within the period of the time to live; and
   providing the certificate of association to the venue.

2. The method of claim 1, wherein the attestation of the user comprises a representation of a biometric sample of the user, the biometric sample of the user obtained in conjunction with collection of the biological sample, the representation generated by a processing device from the obtained biometric sample of the user.

3. The method of claim 2, wherein the biometric sample is one or more of a thumb print set recorded from the user, a retina scan recorded from the user, and a DNA sample obtained from the user and analyzed.

4. The method of claim 3, wherein the certificate comprises the representation of the biometric sample of the user.

5. The method of claim 1, wherein the attestation comprises a video of the user submitting the biological sample, wherein the video is executed under control of a biological sample routine executed to obtain the biological sample.

6. The method of claim 5, wherein the video is witnessed by a trusted agent and the attestation is supplied by the trusted agent.

7. The method of claim 1, wherein the attestation comprises a statement submitted by the user contemporaneously with submission of the biological sample result.

8. The method of claim 1, wherein verifying further comprises computing a probability and a corresponding confidence level that the collected biological sample was obtained from the identified user.

9. The method of claim 1, wherein the access request and the certificate of association are transmitted using end-to-end encryption.

10. The method of claim 9, wherein the end-to-end encryption is implemented using a distributed ledger.

11. The method of claim 10, wherein the distributed ledger is implemented using a blockchain architecture.

12. A health status platform, comprising:
   a receiving component comprising a processor and a data store that receives a test result of a test of a biological sample collected from a human patient, the test result comprising:
      an indication of a presence of an infectious disease in the patient,
      an identification and a verification of the patient from whom the biological sample was collected,
      a location, time and date of sample collection, and
      an identification of the test of the biological sample;
   a certificate component that issues a certificate of origin of the biological sample; and
   a data merging component that cooperates with one or more venue access managers that operate to control access to corresponding venues, the data merging component, comprising:
      a distributed ledger system that stores encrypted test results of the patient and the identification and verification of the patient, and
      an end-to-end encryption system that receives encrypted venue access requests from a venue access manager, decrypts the access requests and determines if the access request is valid or not valid, and for valid access requests, provides an encrypted certificate of origin to the venue access manager.

13. The platform of claim 12, wherein the attestation of the user comprises a representation of a biometric sample of the user, the biometric sample of the user obtained in conjunction with collection of the biological sample, the representation generated by a processing device from the obtained biometric sample of the user.

14. The platform of claim 13, wherein the biometric sample is one or more of a thumb print set recorded from the user, a retina scan recorded from the user, and a DNA sample obtained from the user and analyzed.

15. The platform of claim 14, wherein the certificate comprises the representation of the biometric sample of the user.

16. The platform of claim 12, wherein the attestation comprises a video of the user submitting the biological sample, wherein the video is executed under control of a biological sample routine executed to obtain the biological sample.

17. The platform of claim 16, wherein the video is witnessed by a trusted agent and the attestation is supplied by the trusted agent.

18. The platform of claim 12, wherein the attestation comprises a statement submitted by the user contemporaneously with submission of the biological sample result.

19. The platform of claim 12, wherein the access request and the certificate of association are transmitted using end-to-end encryption, wherein the end-to-end encryption is implemented using a distributed ledger, and wherein the distributed ledger is implemented using a blockchain architecture.

20. A health status system (HSS), comprising:
   a distributed computing system comprising data storage, one or more processors, and wireless and wired communication equipment, the data storage comprising non-transitory-computer-readable media storing a program of instructions that, when executed by a processor, cause the processor to:

receive from a test system a representation of biological sample data of a human sample collected from a human user and analyzed by the test system for an indication of a presence of an infectious disease, and identification information identifying the user, the biological sample data comprising:

the indication of the presence of the infectious disease;

a time and date of sample collection of the biological sample; and an identification of the test system, and the information identifying the identity of the user comprising a representation of biometric sample of the user, the biometric sample obtained in conjunction with collecting the biological sample of the user, store the biological sample data in the data storage;

associate the representation of the biometric sample of the user with the stored biological sample data of the user;

generate a certificate of association between the representation of the biometric sample of the user and the stored biological sample data of the user, comprising the processor:

analyzing the representation of the biometric sample of the user, and based on the analysis, verifying that the collected biological sample data were obtained from the identified user;

receive from a venue, an access request for the user to access the venue;

determine the access request is valid; and provide the certificate of association to the venue.

21. The HSS system of claim 20, wherein the biometric sample is one or more of a thumb print set recorded from the user, a retina scan recorded from the user, and a DNA sample obtained from the user and analyzed.

22. The HSS system of claim 20, wherein the HSS system implements a distributed ledger having a blockchain architecture, and wherein the access request and the certificated are encrypted end to end for transmission using the blockchain architecture.

* * * * *